US009393319B2

(12) United States Patent
Strong et al.

(10) Patent No.: US 9,393,319 B2
(45) Date of Patent: *Jul. 19, 2016

(54) NON-NATURAL RIBONUCLEASE CONJUGATES AS CYTOTOXIC AGENTS

(71) Applicant: Quintessence Biosciences, Inc., Madison, WI (US)

(72) Inventors: Laura E. Strong, Stoughton, WI (US); Peter A. Leland, Fitchburg, WI (US); Thomas Burke, Madison, WI (US)

(73) Assignee: Quintessence Biosciences, Inc., Madison, WI (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/252,475

(22) Filed: Apr. 14, 2014

(65) Prior Publication Data

US 2014/0212946 A1 Jul. 31, 2014

Related U.S. Application Data

(62) Division of application No. 13/923,008, filed on Jun. 20, 2013, now Pat. No. 8,697,065, which is a division of application No. 11/105,041, filed on Apr. 13, 2005, now Pat. No. 8,470,315.

(60) Provisional application No. 60/561,609, filed on Apr. 13, 2004.

(51) Int. Cl.

| | |
|---|---|
| ***A61K 38/46*** | (2006.01) |
| ***A61K 38/47*** | (2006.01) |
| ***A61K 47/48*** | (2006.01) |
| ***C12N 9/22*** | (2006.01) |
| ***C12N 9/14*** | (2006.01) |
| ***C07H 21/04*** | (2006.01) |
| ***C07K 16/28*** | (2006.01) |
| ***C07K 16/30*** | (2006.01) |
| ***C07K 16/18*** | (2006.01) |
| ***C12N 9/12*** | (2006.01) |

(52) U.S. Cl.

CPC ......... *A61K 47/48569* (2013.01); *A61K 38/465* (2013.01); *A61K 47/4843* (2013.01); *C07K 16/18* (2013.01); *C07K 16/2803* (2013.01); *C07K 16/3061* (2013.01); *C12N 9/12* (2013.01)

(58) Field of Classification Search

None

See application file for complete search history.

(56) References Cited

U.S. PATENT DOCUMENTS

| | | | |
|---|---|---|---|
| 4,424,311 | A | 1/1984 | Nagaoka |
| 4,708,930 | A | 11/1987 | Kortright |
| 4,743,543 | A | 5/1988 | Kortright |
| 4,892,935 | A | 1/1990 | Yoshida |
| 4,914,021 | A | 4/1990 | Toth |
| 4,918,164 | A | 4/1990 | Hellstrom |
| 4,921,789 | A | 5/1990 | Salem |
| 4,921,790 | A | 5/1990 | O'brien |
| 4,939,240 | A | 7/1990 | Chu |
| 4,963,484 | A | 10/1990 | Kufe |
| 5,053,489 | A | 10/1991 | Kufe |
| 5,096,815 | A | 3/1992 | Ladner et al. |
| 5,110,911 | A | 5/1992 | Samuel |
| 5,198,346 | A | 3/1993 | Ladner et al. |
| 5,200,182 | A | 4/1993 | Kiczka |
| 5,223,409 | A | 6/1993 | Ladner et al. |
| 5,270,163 | A | 12/1993 | Gold |
| 5,270,204 | A | 12/1993 | Vallee et al. |
| 5,286,487 | A | 2/1994 | Vallee et al. |
| 5,286,637 | A | 2/1994 | Veronese et al. |
| 5,359,030 | A | 10/1994 | Ekwuribe |
| 5,389,537 | A | 2/1995 | Raines et al. |
| 5,446,090 | A | 8/1995 | Harris |
| 5,475,096 | A | 12/1995 | Gold |
| 5,512,443 | A | 4/1996 | Schlom |
| 5,545,530 | A | 8/1996 | Satomura |
| 5,559,212 | A | 9/1996 | Ardelt |
| 5,562,907 | A | 10/1996 | Arnon |
| 5,660,827 | A | 8/1997 | Thorpe et al. |
| 5,672,662 | A | 9/1997 | Harris |
| 5,693,763 | A | 12/1997 | Codington |
| 5,733,731 | A | 3/1998 | Schatz et al. |
| 5,739,208 | A | 4/1998 | Harris |
| 5,786,457 | A | 7/1998 | Nett et al. |
| 5,808,005 | A | 9/1998 | Codington |
| 5,811,238 | A | 9/1998 | Stemmer et al. |
| 5,824,544 | A | 10/1998 | Armentano et al. |
| 5,824,784 | A | 10/1998 | Kinstler |
| 5,830,721 | A | 11/1998 | Stemmer et al. |

(Continued)

FOREIGN PATENT DOCUMENTS

| | | |
|---|---|---|
| CN | 101268186 | 9/2008 |
| EP | 1316318 | 6/2003 |

(Continued)

OTHER PUBLICATIONS

Pouckova et al., "Some biological actions of PEG-conjugated Rnase A oligomers." Neoplasma, Jan. 1, 2006, 53(1):79-85.

(Continued)

*Primary Examiner* — Iqbal H Chowdhury

(74) *Attorney, Agent, or Firm* — Casimir Jones, S.C.; David Casimir

(57) ABSTRACT

The present invention is directed toward the delivery of a toxic protein to pathogenic cells, particularly cancer cells. In preferred embodiments, the toxic protein is a ribonuclease that has been modified to make it toxic to target cells and that can be conjugated to a target cell-specific delivery vector, such as an antibody, for delivery to pathogenic cells.

17 Claims, 2 Drawing Sheets

(56) References Cited

U.S. PATENT DOCUMENTS

| | | | |
|---|---|---|---|
| 5,830,730 | A | 11/1998 | German et al. |
| 5,837,458 | A | 11/1998 | Minshull et al. |
| 5,840,296 | A | 11/1998 | Raines et al. |
| 5,840,840 | A | 11/1998 | Rybak et al. |
| 5,855,866 | A | 1/1999 | Thorpe |
| 5,866,119 | A | 2/1999 | Bandman et al. |
| 5,872,154 | A | 2/1999 | Wilson et al. |
| 5,885,808 | A | 3/1999 | Spooner et al. |
| 5,892,019 | A | 4/1999 | Schlom |
| 5,892,020 | A | 4/1999 | Mezes |
| 5,900,461 | A | 5/1999 | Harris |
| 5,932,462 | A | 8/1999 | Harris |
| 5,955,073 | A | 9/1999 | Rybak et al. |
| 5,981,225 | A | 11/1999 | Kochanek et al. |
| 5,990,237 | A | 11/1999 | Bentley |
| 5,994,106 | A | 11/1999 | Kovesdi et al. |
| 5,994,128 | A | 11/1999 | Fallaux et al. |
| 5,994,132 | A | 11/1999 | Chamberlain et al. |
| 6,001,557 | A | 12/1999 | Wilson et al. |
| 6,019,978 | A | 2/2000 | Ertl et al. |
| 6,033,908 | A | 3/2000 | Bout et al. |
| 6,045,793 | A | 4/2000 | Rybak et al. |
| 6,051,230 | A | 4/2000 | Thorpe et al. |
| 6,077,499 | A | 6/2000 | Griffiths et al. |
| 6,083,477 | A | 7/2000 | Goldenberg |
| 6,183,744 | B1 | 2/2001 | Goldenberg |
| 6,197,528 | B1 | 3/2001 | Wu et al. |
| 6,214,966 | B1 | 4/2001 | Harris |
| 6,271,369 | B1 | 8/2001 | Torrence et al. |
| 6,280,991 | B1 | 8/2001 | Raines |
| 6,312,694 | B1 | 11/2001 | Thorpe et al. |
| 6,348,558 | B1 | 2/2002 | Harris |
| 6,362,254 | B2 | 3/2002 | Harris |
| 6,362,276 | B1 | 3/2002 | Harris |
| 6,395,276 | B1 | 5/2002 | Rybak et al. |
| 6,399,068 | B1 | 6/2002 | Goldenberg |
| 6,406,897 | B1 | 6/2002 | Kim et al. |
| 6,416,758 | B1 | 7/2002 | Thorpe et al. |
| 6,428,785 | B1 | 8/2002 | Gokcen |
| 6,432,397 | B1 | 8/2002 | Harris |
| 6,437,025 | B1 | 8/2002 | Harris |
| 6,448,369 | B1 | 9/2002 | Bentley |
| 6,515,100 | B2 | 2/2003 | Harris |
| 6,541,543 | B2 | 4/2003 | Harris |
| 6,541,619 | B1 | 4/2003 | Park et al. |
| 6,610,281 | B2 | 8/2003 | Harris |
| 6,649,383 | B1 | 11/2003 | Cheung |
| 6,649,393 | B1 | 11/2003 | Youle et al. |
| 6,653,104 | B2 | 11/2003 | Goldenberg |
| 6,664,331 | B2 | 12/2003 | Harris |
| 6,676,941 | B2 | 1/2004 | Thorpe et al. |
| 6,737,505 | B2 | 5/2004 | Bentley |
| 6,828,401 | B2 | 12/2004 | Nho |
| 6,838,076 | B2 | 1/2005 | Patton |
| 6,864,327 | B2 | 3/2005 | Bentley |
| 6,864,350 | B2 | 3/2005 | Harris |
| 6,894,025 | B2 | 5/2005 | Harris |
| 6,962,702 | B2 | 11/2005 | Hansen et al. |
| 7,033,572 | B2 | 4/2006 | Goldenberg |
| 7,125,541 | B2 | 10/2006 | Thorpe et al. |
| 7,199,223 | B2 | 4/2007 | Bossard |
| 7,355,019 | B2 | 4/2008 | Backer et al. |
| 7,416,875 | B2 | 8/2008 | Raines et al. |
| 7,476,725 | B2 | 1/2009 | Zaplisky |
| 8,003,111 | B2 | 8/2011 | Chang et al. |
| 8,029,782 | B2 | 10/2011 | Klink et al. |
| 8,216,567 | B2 | 7/2012 | Klink et al. |
| 2001/0049434 | A1 | 12/2001 | Conklin et al. |
| 2002/0006379 | A1 | 1/2002 | Hansen et al. |
| 2002/0037289 | A1 | 3/2002 | Thorpe et al. |
| 2002/0048550 | A1 | 4/2002 | Vallera et al. |
| 2002/0106359 | A1 | 8/2002 | Gokcen |
| 2002/0119153 | A1 | 8/2002 | Thorpe et al. |
| 2002/0187153 | A1 | 12/2002 | Goldenberg |
| 2003/0031669 | A1 | 2/2003 | Goldenberg |
| 2003/0114368 | A1 | 6/2003 | Rybak |
| 2003/0219785 | A1 | 11/2003 | Hallahan et al. |
| 2005/0158273 | A1 | 7/2005 | Harris |
| 2005/0181449 | A1 | 8/2005 | Kozlowski |
| 2005/0221431 | A1 | 10/2005 | Backer et al. |
| 2005/0261232 | A1 | 11/2005 | Strong et al. |
| 2005/0287113 | A1 | 12/2005 | Zaplisky |
| 2006/0292137 | A1 | 12/2006 | Raines et al. |
| 2007/0166278 | A1 | 7/2007 | Veronese |
| 2008/0025964 | A1 | 1/2008 | Kink |
| 2008/0095755 | A1 | 4/2008 | Kink |
| 2013/0078229 | A1 | 3/2013 | Kink et al. |

FOREIGN PATENT DOCUMENTS

| | | | |
|---|---|---|---|
| JP | 2003-206236 | | 7/2003 |
| WO | 91/01758 | | 2/1991 |
| WO | 9621469 | | 7/1996 |
| WO | 97/38134 | | 10/1997 |
| WO | 98/33941 | | 8/1998 |
| WO | 99/02685 | | 1/1999 |
| WO | 99/07724 | | 2/1999 |
| WO | 00/09675 | | 2/2000 |
| WO | 00/12738 | | 3/2000 |
| WO | 00/31242 | | 6/2000 |
| WO | 01/94547 | | 12/2001 |
| WO | 02/25630 | | 1/2002 |
| WO | 03/031581 | | 4/2003 |
| WO | 2006/138558 | A2 | 12/2006 |
| WO | 2007/149594 | | 12/2007 |
| WO | 2008/010991 | A2 | 1/2008 |

OTHER PUBLICATIONS

Asai, T. et al. “An interaction between S tag and S protein derived from human ribonuclease 1 allows site-specific conjugation of an enzyme to an antibody for targeted drug delivery,” 2005 J Immun Meth, 299:63-76.

Backer M et al., “Adapter Protein for Site-Specific conjugation of Payloads for Targeted Drug Delivery,” 2004 Bioconjugate Chem 15:1021-9.

Backer, M.V. et al., 2003, “Humanized docking system for assembly of targeting drug delivery complexes,” J Cont Release, 89:499-511.

Bal, H., et al, “Human pancreatic ribonuclease Deletion of the carboxyl-terminal EDST extension enhances ribonuclease activity and thermostability,” Eur. J. Biochem., 245, pp. 465-469 (1997).

Ban et al., “Interface Surfaces for Protein-Protein Complexes”, Proc. 8th Ann. Intl. Conf. Res. Comp. Mol.Biol., (2004) pp. 205-212.

Benito, A., et al., “Stabilization of human pancreatic ribonuclease through mutation at its N-terminal edge,” Protein Eng., 15, pp. 887-893 (2002).

Binkley et al., “RNA ligands to human nerve growth factor ,” 1995 Nuc Acids Res 23(16):3198-205.

Boix E., et al., “Crystal Structure of Eosinophil Cationic Protein at 2.4 A Resolution,” Biochemistry, (1999) 38, pp. 16794-16801.

Bosch, M., et al., “A Nuclear Localization Sequence Endows Human Pancreatic Ribonuclease with Cytotoxic Activity,” Biochemistry, 43, pp. 2167-2177 (2004).

Bretscher, Leland, et al., “A Ribonuclease A variant with low catalytic activity but potent cytotoxic activity,” J Biol. Chem., (2000) 275, 9893-9896.

Cadwell R.C., et al., “Randomization of Genes by PCR Mutagenesis,” PCR Methods and Applications, (1992) 1(4), pp. 28-33.

Capala et al., “Boronated Epidermal Growth Factor as a Potential Targeting Agent for Boron Neutron Capture Therapy of Brain Tumors,” 1996 Bioconjugate Chem 7:7-15.

Crameri A., et al., “Improved Green Flourescent Protein by Molecular Evolution,” Nature Biotechnology, (1996)14, pp. 315-319.

Crameri A., et al., “Molecular evolution of an arsenate detoxification pathway by DNA shuffling,” Nature Biotechnology, (1997) 15, pp. 436-438.

Curran, T.P., et al., “Alteration of the Enzymatic Specificity of Human Angiogenin by Site-Directed Mutagenesis,” Biochemistry 32, pp. 2307-2313 (1993).

(56) References Cited

OTHER PUBLICATIONS

Cwirla S., et al., "Peptides onphage: A vast library of peptides for identifying ligands," Proc. Natl. Acad. Sci., (1990) 87, pp. 6378-6382.
Davis et al., Basic Methods in Molecular Biology. (1986).
De Lorenzo, C., "A Fully Human Antitumor ImmunoRNase Selective for ErbB-2-Positive Carcinomas," Cancer Res., (2004) 64, pp. 4870-4874.
Del Cardayre & Raines, "Structural Determinants of Enzymatic Processivity", 1994 Biochem 33:6031-6037.
Deonarain, M.P. et al., "Targeting enzymes for cancer therapy: Old Enzymes in New Roles." British Journal of Cancer, Nov. 1994 70(5):786-794.
Dermer, GB, "Another Anniversary for the War on Cancer," Bio/Technology. Mar. 12, 1994, p. 320.
Devlin J., et al., "Random Peptide Libraries: A source of specific protein Binding molecules," Science, (1990) 249, 404-406.
Dharap, S.S. et al., "Molecular Targeting of Drug Delivery Systems to Ovarian Cancer . . . " Journal of Controlled Release, (2003) 91, pp. 61-73.
Di Gaetano, G., et al., "Second generation antitumour human RNase: significance of its structural and functional features for the mechanism of antitumour action," Biochem. J., 358, pp. 241-247 (2001).
Dickson, K A, et al., "Compensating effects on the cytotoxicity of ribonuclease A variants," 2003 Archives Biochem and Biophysics, Acad Press, 415:172-177.
Domachowske et al., "Evolution of antiviral activity in the ribonuclease A gene superfamily . . . ," Nucleic Acids Res 26 (23): 5327-32 (1998).
Eckert K., et al., "DNA Polymerase Fidelity and the Polymerase Chain Reaction," PCR Methods and Applications, (1991) 1(1), pp. 17-24.
Fisher, B.M., et al., "Coulombic Forces in Protein-RNA Interactions: Binding and Cleavage by Ribonuclease A and Variants at Lys7, Arg10, and Lys66," Biochemistry, 37, pp. 12121-12132 (1998).
Francis et al., Stability of protein pharmaceuticals: in vivo pathways of degradation and strategies for protein stabilization (Eds. Ahern., T. and Manning, M.C.) Plenum, N. Y., pp. 247-251 (1991).
Futami J., et al., "Inhibition of cell growth by a fused protein of human ribonuclease 1 and human basic fibroblast growth factor" Protein Engineering, (1999) 12(11) pp. 1013-1018.
Gaur, D. et al., "Interaction of human pancreatic ribonuclease with human ribonuclease inhibitor. Generation of inhibitor-resistant cytotoxic variants," J. Biol. Chem., 276:24978-24984 (2001).
Gluzman Y., "SV40-transformed Simian Cells Support the Replication of Early SV40 Mutants," Cell, (1981) 23, pp. 175-182.
Goldberg and Baldwin, "A specific transition state for S-peptide combining with folded S-protein and then refolding," 1999 PNAS 96:2019-2024.
Gorman, C., et al. "The Hype and the Hope" Time. 1998, 151(19) pp. 40-44.
Gura, T., "Systems for Identifying New Drugs are Often Faulty," Science. 1997, 278(Nov. 7), pp. 1041-1042.
Gutte B., et al., "The synthesis of ribonuclease A," Journal of Biological Chemistry, (1971) 246(6), pp. 1922-1941.
Haldar et al., "Bcl2 is the Guardian of Microtubule Integrity," 1997 Cancer Research 57:229-233.
Hamachi et al., "Design and semisynthesis of spermine-sensitive ribonucleases S'" 1999 Bioorg Med Chem Lett 9:1215-1218.
Hanisch et al., "Structural studies on oncofetal carbohydrate antigens (Ca 19-9, Ca 50, and Ca 125) carried by O-linked sialyloligosaccharides on human amniotic mucins," 1988 Carbohydr Res 178:29-47.
Harder J., et al, "RNase 7, a Novel Innate Immune Defense Antimicrobial Protein of Healthy Human skin," J. Biol. Chem., (2002) 277, pp. 46779-46784.
Hinoda et al., "Immunochemical characterization of adenocarcinoma-associated antigen yh206," 1988 Cancer J 42:653-658.
Hursey, M., et al., "Specifically Targeting the CD22 Receptor of Human B-Cell Lymphomas With RNA . . . " Leukemia & Lymphoma, (2002) 43(5), pp. 953-959.
Ike Y., et al., "Solid phase synthesis of polynucleotides," Nucleic Acids Research, (1983) 11(2), pp. 477-488.
Ishida et al., "Related Glycoproteins from Normal Secretory and Malignant Breast Cells," 1989 Tumor Biol 10:12-22.
Itakura K., et al., "Chemical Synthesis . . . " Recombinant DNA, in Walton (ed.),Proceedings of 3rd Cleveland Symposium, (1981) pp. 273-289.
Itakura K., et al., "Synthesis and Use of Synthetic Oligonucleotides," Ann. Rev. Biochem., (1984) 53, pp. 323-356.
Iyer S., et al, "Molecular Recognition of Human Eosinophil-derived Neurotoxin (RNase 2) by Placental Ribonuclease Inhibitor," J Mol. Biol., (2005) 347, pp. 637-655.
Jellinek et al., "Inhibition of receptor binding by high-affinity RNA ligands to vascular endothelial growth factor," 1994 Biochem 33(34):10450-6.
Jinno H., et al., "Epidermal Growth Factor Receptor-Dependent Cytotoxicity for Human Squamous Carcinoma Cell Lines . . . ," Life Sciences, (1996) 58(21), pp. 1901-1908.
Jinno U.H., et al., "Epidermal growth factor receptor-dependent cytotoxic effect by an EGF-ribonuclease conjugate . . . " Cancer Chemotherapy and Pharmacology, (1996) 38(4), pp. 303-308.
Kelemen et al., "Hypersensitive substrate for ribonucleases", 1999 Nucl Acids Res, 27: 3696-3701.
Kinstler et al., "Mono-N-terminal poly(ethylene glycol)—protein conjugates," 2002 Advanced Drug Delivery Reviews 54:477-485.
Kirpotin et al., "Sterically Stabilized Anti-HER2 Immunoliposomes: Design and Targeting to Human Breast Cancer Cells in Vitro," 1997 Biochem 36:66.
Kjeldsen et al., "Preparation and Characterization of Monoclonal Antibodies Directed to the Tumor-associated O-linked Sialosyl-2- . . . ," 1988 Cancer Res 48:2214-2220.
Klink ,T A, et al., "Conformational stability is a determinant of ribonuclease A cytoxicity," 2000, J Biolog Chem, 275:17463-17467.
Kobe, et al., "Mechanism of ribonuclease inhibition by ribonuclease inhibitor protein based on the crystal structure of its complex with ribonuclease A," J Mol Biol, 1996, 264:1028-43.
Kozlowski A, et al., "Development of pegylated interferons for the treatment of chronic hepatitis C." 2001 BioDrugs, 15:419-429.
Krasnykh V, et al., "Characterization of an Adenovirus Vector Containing a Heterologous Peptide Epitope in the HI Loop of the Fiber Knob," J Virology, (1998) 72, pp. 1844-1852.
Lan et al., "Isolation and properties of a human pancreatic adenocarcinoma-associated . . . ," 1985 Cancer Res 45:305-310.
Lanni et al., "p53-independent apoptosis induced by paclitaxel through an indirect mechanism," 1997 Proc Natl Acad Sci 94:9679-9683.
Lavis et al., "Tuning the pKa of Flourescein to Optimize Binding Assays," 2007 Anal Chem, 79:6775-6782.
Laznicek, et al. "Pharmacokinetics and Distribution of Ribonuclease and its Monomethoxypoly(Ethylene Glycol) Derivatives in Rats" Pharmacological Research, vol. 28, No. 2, Sep. 1, 1993, pp. 153-162.
Leland, P.A. et al., "Cancer Chemotherapy—Ribonucleases to the Rescue," Chem and Biology. Apr. 2001, 8:405-413.
Leland, P.A., et al., "Endowing Human Pancreatic Ribonuclease with Toxicity for Cancer Cells," Journal of Biological Chemistry, (2001) 276(46), pp. 43095-43102.
Pous J., et al, "Three-dimensional Structure of a Human Pancreatic Ribonuclease Variant, a Step Forward in the Design of Cytotoxic Ribonucleases," J Mol. Biol., (2000) 303, pp. 49-60.
Leland, P.A., et al., "Ribonuclease A Variants with Potent Cytotoxic Activity," Proc. Natl. Acad. Sci., 95, pp. 10407-10412 (1998).
Leonidas D.D., et al, "Binding of phosphase and pyrophosphate isons at the active site of human angiogenin as revealed by X-ray crystallography," Protein Sci., (2001) 10, pp. 1669-1676.
Leung D., et al., "A Method for Random Mutagenesis of a defined DNA Segment using . . . ," Technique, (1989) 1(1), pp. 11-15.
Lin, M.C., "The Structural Roles of Amino Acid Residues Near the Carboxyl Terminus of Bovine Pancreatic Ribonuclease A," J. Biol. Chem., 245, pp. 6726-6731 (1970).

(56) References Cited

OTHER PUBLICATIONS

Mallorqui-Fernandez, G., et al., "Three-dimensional Crystal Structure of Human Eosinophil Cationic Protein (RNase 3) at 1.75 A Resolution," J. Mol. Biol., (2000) 300, pp. 1297-1307.
Matousek et al. "PEG chains increase aspermatogenic and antitumor activity of RNase A and BS-RNase enzymes" Journal of Controlled Release 82 (2002) 29-37.
Matousek J, "Ribonucleases and their antitumor activity," 2001, Comp Biochem Physiology Tox Pharma, 129, pp. 175-191.
Matousek, et al. "Effect of hyaluronidase and PEG chain conjugation on the biologic and antitumor activity of RNase A" Journal of Controlled Release, vol. 94, No. 2-3, Feb. 10, 2004, pp. 401-410.
McGrath M., et al., "Immunotoxin Resistance in Multidrug Resistant Cells," Cancer Research, (2003) 63, pp. 72-79.
McKie, R., "Cancer Research Set Back a Decade," The Observer. 2001, (Jun. 10), pp. 1-4.
McLane K, "Transplantation of a 17-amino acid a-helical DNA-binding domain into an antibody molecule confers sequence-dependent DNA recognition," Proc. Natl. Acad. Sci., (1995) 92, pp. 5214-5218.
Merlino, A., et al., "The importance of Dynamic Effects on the Enzyme Activity X-ray Structure and Molecular Dynamics of Onconase Mutants," J Biol Chem 2005, 280:17953-17960.
Michaelis, et al. "Coupling of the antitumoral enzyme bovine seminal ribonuclease to polyethylene glycol chains increases its systemic efficacy in mice" Anti-Cancer Drugs, vol. 13, No. 2, Feb. 2002, pp. 149-154.
Miller, K.D. and Sledge, G.W. Jr, "Taxanes in the treatment of breast cancer: a prodigy comes of age," 1999 Cancer Investigation, 17:121-136.
Milton Harris J et al: "Effect of Pegylation on Pharmaceuticals" Nature Reviews. Drug Discovery, vol. 2, No. 3, Mar. 1, 2003, pp. 214-221.
Mitchell et al., "Interfaces in Molecular Docking," Molec. Simul. (2004) 30, pp. 97-106.
Mohan C.G., et al, "The Crystal Structure of Eosinophil Cationic Protein in Complex with 2',5'-ADP at 2.0 A Resolution Reveals the Details of the Ribonucleolytic Active Site," Biochemistry, (2002) 41, pp. 12100-12106.
Moore J., et al., "Directed evolution of a para-nitrobenzyl esterase for aqueous-organic solvents," Nature Biotechnology, (1996) 14, pp. 458-467.
Mosimann S.C., et al, "X-ray Crystallographic Structure of Recombinant Eosinophil-derived Neurotoxin at 1.83 A Resolution," J. Mol. Biol., (1996) 260, pp. 540-552.
Narang S., "DNA Synthesis," Tetrahedron Report, (1983) 39(1), pp. 3-22.
Newton, D.L., et al., "Cytotoxic Ribonuclease Chimeras Tergeted Tumoricidal Activity in-vitro and in-vivo," Journal of Biological Chemistry, (1992) 267(27), pp. 19572-19578.
Newton, D.L., et al., "Potent and specific antitumor effects of an anti-CD22-targeted cytotoxic ribonuclease . . . " Blood, (2001) 97(2), pp. 528-535.
Nguyen, D.M., et al., "Impact of Transfusion of Mediastinal Shed Blood on Serum Levels of Cardiac Enzymes," Ann. Thorac. Surg. 1996, 62, pp. 109-114.
Ottl et al., "Preparation and Photoactivation of Caged Fluorophores and Caged Proteins Using a New Class of Heterobifunctional, Photocleavable Cross-Linking Reagents,"1998 Bioconj Chem 9:143-151.
Papageorgiou A.C., et al., "Molecular recognition of human angiogenin by placental ribonuclease inhibitor—an X-ray crystallographic study at 2.0 Å resolution," EMBO J., (1997) 16, pp. 5162-5177.
Pouckova, et al. "Polymer-conjugated bovine pancreatic and seminal ribonucleases inhibit growth of human tumors in nude mice" Journal of Controlled Release, vol. 95, No. 1, Feb. 20, 2004, pp. 83-92.
Park et al., "Anti-HER2 immunoliposomes for targeted therapy of human tumors," 1997 Cancer Lett 118:153-160.
Pegram et al., "Phase II Study of Intravenous Recombinant Humanized Anti-p185 HER-2 Monoclonal Antibody (rhuMAb HER-2) Plus Cisplatin in Patients with HER-2/NEU Overexpressing Metastatic Breast Cancer", 1995 Am Soc Clin Oncol 14:106.
Piccoli, Renate et al., "A dimeric mutant of human pancreatic ribonuclease with selective cytotoxicity toward malignant cells," 1999, Pro Nat Acad Sci, 96, pp. 7768-7773.
Potenza, N, et al., "Hybridase activity of human ribonuclease-1 revealed by a real-time fluorometric assay," Nucleic Acids Res, 2006, 34(10), pp. 2906-2913.
Zaffaroni et al., "Induction of apoptosis by taxol and cisplatin and effect on cell cycle-related proteins in cisplatin-sensitive and -resistant human ovarian cancer cells," 1998 Brit. J. Cancer 77:1378-1385.
Rutkoski et al., "Disruption of Shape-Complementarity Markers to Create Cytotoxic Variants of Ribonucleases A". J Molecular Biology 2005, 354(1): 41-54.
Itakura et al., "Expression of *E.Coli* of a Chemically Systhesized Gene for the hormone Somatostatin." Science 1984, 198: 1056.
Jinno H., et al., "The Cytotoxicity of a Conjugate Composed of Human Epidermal Growth Factor," Anticancer Res., (2002) 22, pp. 4141-4146.
Monfardini et al., "A Branched Monomethoxypoly(ethylene glycol) for Protein Modification" Bioconjugate Chem. 1995, 6(1): 62-69.
Pous J., et al, "Three-dimensional structure of human RNase 1AN7 at 1.9 A resolution," Acta Crystallogr D Biol Crystallogr., (2001) 57, pp. 498-505.
Press et al., "Expression of the HER-2/neu proto-oncogene in normal human adult and fetal tissues," 1990 Oncogene 5:953-62.
Psarras, K, et al., "Human pancreatic RNase1-human epidermal growth factor fusion: An entirely human immunotoxin analog with cytotoxic properties against squamous cell carcinomas," Protein Eng, 1998, 11:1285-92.
Raines, R.T., et al., "A New Remote Subsite in Ribonuclease A," J. Biol. Chem, 273, pp. 34134-34138 (1998).
Reddi, K.K., "Nature and Origin of Human Serum Ribonuclease" Biochem. Biophys. Res. Commun. 1975, 67(1), pp. 110-118.
Ribo, M., et al., "Heterogeneity in the Glycosylation Pattern of Human Pancreatic Ribonuclease," Biol. Chem. Hoppe-seyler, 375, pp. 357-363 (1994).
Roberts B., et al., "Directed evolution of a protein: Selection of potent . . . " Proc. Natl. Acad. Sci., (1992) 89, pp. 2429-2433.
Roberts et al. "Chemistry for peptide and protein PEGylation," 2002 Advanced Drug Delivery Reviews 54:459-476.
Roehrl et al., "A General Framework for Development and Data Analysis of Competitive High-Throughput Screens for Small-Molecule Inhibitors of Protein-Protein Interactions by Fluorescence Polarization," 2004 Biochem 43:16056-16066.
Rosenberg H F et al., "Eosinophils, Eosinophil Ribonucleases, and their Role in Host Defense Against Respiratory Virus Pathogens," 2001, J Leukocyte Bio, Fed Am Soc Exper Bio, 70, pp. 691-698.
Rosenberg H, et al, "Molecular cloning and characterization of a novel human ribonuclease (RNase k6): increasing diversity in the enlarging ribonuclease gene family," Nucleic Acids Research, (1994) 24, pp. 3507-3513.
Rybak S., et al., "Rational Immunotherapy With Ribonuclease Chimeras," Cell Biophysics, (1992) 21(1-3), pp. 121-138.
Rybak, S., et al., "Cytotoxic Potential of Ribonuclease and Ribonuclease Hybrid Proteins," Journal of Biological Chemistry, (1991) 266(31), pp. 21202-21207.
Scott J., et al., "Searching for peptide ligands with an Epitope library," Science, (1990) 249, pp. 386-390.
Shapiro, R., et al., "Analysis of the Interactions of Human Ribonuclease Inhibitor with Angiogenin and Ribonuclease A by Mutagenesis: Importance of Inhibitor Residues Inside versus Outside the C-terminal "Hot Spot"," J. Mol. Biol., 302, pp. 497-519 (2000).
Skerra, et al., "Engineered protein scaffolds for molecular recognition," J Mol Recognit. 2000, 13:167-87.
Smith G., "The progeny of sexual PCR," Nature, (1994) 370, pp. 324-325.
Smith et al., "Potent Inhibition of Ribonuclease A by Oligo(vinylsulfonic Acid)", 2003 J Biol Chem 278:20934-30938.

(56) References Cited

OTHER PUBLICATIONS

Sorrentino and Glitz, "Ribonuclease activity and substrate preference of human eosinophil cationic protein (ECP)"1991 FEBS Lett. 288:23-6.
Sorrentino, S., et al., "Degradation of Double-Stranded RNA by Human Pancreatic Ribonuclease: Crucial Role of Noncatalytic BasicAmino Acid Residues," Biochemistry 42, pp. 10182-10190 (2003).
Springer, et al., "Blood group Tn-active macromolecules from human carcinomas and erythrocytes: characterization of and specific reactivity with mono- and poly-clonal anti-Tn antibodies induced by various immunogens," 1988 Carbohydr Res 178:271-292.
Stemmer W., "DNA shuffling by random fragmentation and reassembly . . . ," Proc. Natl. Acad. Sci., (1994) 91, pp. 10747-10751.
Stemmer W., "Rapid evolution of a protein in vitro by DNA shuffling," Nature, (1994) 370, pp. 389-391.
Strong, L E et al., "408 Poster Human RNase 1 variants are effective anti-cancer agents," 2006, EP J Cancer Supp, Pergamon, Oxford, GB, 4, p. 125.
Strong, Laura E, et al., "Human ribonuclease variants with broad anti-cancer activity," 2006, Am Assoc for Cancer Res Annual Mtg, 47, P514.
Stryer L., "Introduction of Proteins," Biochemistry, 2nd Edition,(1981) pp. 17-21.
Suzuki M., et al., "Engineering receptor-mediated cytotoxicity into human ribonucleases . . . ," Nature Biotechnology, (1999) 17, pp. 265-270.
Swaminathan G., et al, "Atomic Resolution (0.98 A) Structure of Eosinophil-Derived Neurotoxin," Biochemistry, (2002) 41, pp. 3341-3352.
Terzyan S.S., "The Three-dimensional Structure of Human RNase 4, Unliganded and Complexed with d(Up), Reveals the Basis for its Uridine Selectivity", et al, J Mol. Biol., (1999) 285, pp. 205-214.
Tjandra, et al., "Application of mammary serum antigen assay in the management of breast cancer: A preliminary report," 1988 J Surg 75:811-817.
Tortora et al., "Synergistic Inhibition of Growth and Induction of Apoptosis by 8-Chloro-cAMP and Paclitaxel or Cisplatin in Human Cancer Cells," 1997 Cancer Res 57:5107-5111. X.
Trautwein, K. et al., "Site-directed mutagenesis of bovine pancreatic ribonuclease: lysine-41 and aspartate-121," FEBS Lett., 281, pp. 275-277 (1991).
Tuerk et al., "In vitro evolution of functional nucleic acids : high-affinity RNA ligands of HIV-1 proteins," 1993 Gene 137:33-9.
Vasey et al., "Phase I Clinical and Pharmacokinetic Study of PK1 [N-(2-Hydroxypropyl) methacrylamide Copolymer Doxorubicin] . . . ," 1999 Clin Cancer Res 5:83-94.
Veronese I "Surface Modification of Proteins" Applied Biochemistry and Biotechnology, vol. 11, 1985, pp. 141-152.
Veronese II "Peptide and protein PEGylation: a review of problems and solutions" Biomaterials 22 (2001) 405-417.
Wang, "An exact mathematical expression for describing competitive binding of two different ligants to a protein molecule", 1995 FEBS Lett 360: 111-114.
Yamamura, t., et al., "Immunosuppressive and Anticancer Effect of a Mammalian Ribonuclease that Targets High-affinity Interleukin-2 receptors," European Journal of Surgery, (2002) 168(1), pp. 49-54.
Zalipsky, "Functionalized Poly(ethylene glycol) for Preparation of Biologically Relevant Conjugates," Bioconjugate Chem 6, 150-165 (1995).
Zhang J., et al, "Human RNase 7: a new cationic ribonuclease of the RNase A superfamily," Nucleic Acids Res., (2003) 31, pp. 602-607.
Zhang J., et al, "RNase 8, a Novel RNase A Superfamily Ribonuclease Expressed Uniquely in Placenta," Nucleic Acids Res., (2002) 30, pp. 1169-1175.
Zhang J., et al., "Directed evolution of a fucosidase from a galatosidase by DNA shuffling and screening," Proc. Natl. Acad. Sci., (1997) 94, pp. 4504-4509.
Zhao H., et al., "Optimization of DNA shuffling for high fidelity recombination," Nucleic Acids Research,(1997) 25(6), pp. 1307-1308.
Zhou, et al., "Selection of Antibiotic-Resistant Bacterial Mutants: Allelic Diversity among Fluoroquinolone-Resistant Mutations," 2000 JID 182:517-525.
Yagi et al., "Anti-tumor effect in an in vivo model by human-derived pancreatic RNase with basic fibroblast growth factor insertional fusion protein through antiangiogenic properties." Cancer Sci. Dec. 2006;97(12):1315-20.
Hait et al., "Sensitivity of K562 human chronic myelogenous leukemia blast cells transfected with a human multidrug resistance cDNA to cytotoxic drugs and differentiating agents." J Clin Invest. May 1993;91(5):2207-15.

A.

B.

SEQUENCE LISTING

```
<160> NUMBER OF SEQ ID NOS: 2

<210> SEQ ID NO 1
<211> LENGTH: 124
<212> TYPE: PRT
<213> ORGANISM: Bos taurus

<400> SEQUENCE: 1

Lys Glu Thr Ala Ala Ala Lys Phe Glu Arg Gln His Met Asp Ser Ser
1               5                   10                  15

Thr Ser Ala Ala Ser Ser Ser Asn Tyr Cys Asn Gln Met Met Lys Ser
            20                  25                  30

Arg Asn Leu Thr Lys Asp Arg Cys Lys Pro Val Asn Thr Phe Val His
        35                  40                  45

Glu Ser Leu Ala Asp Val Gln Ala Val Cys Ser Gln Lys Asn Val Ala
    50                  55                  60

Cys Lys Asn Gly Gln Thr Asn Cys Tyr Gln Ser Tyr Ser Thr Met Ser
65                  70                  75                  80

Ile Thr Asp Cys Arg Glu Thr Gly Ser Ser Lys Tyr Pro Asn Cys Ala
                85                  90                  95

Tyr Lys Thr Thr Gln Ala Asn Lys His Ile Ile Val Ala Cys Glu Gly
            100                 105                 110

Asn Pro Tyr Val Pro Val His Phe Asp Ala Ser Val
        115                 120


<210> SEQ ID NO 2
<211> LENGTH: 128
<212> TYPE: PRT
<213> ORGANISM: Homo sapiens

<400> SEQUENCE: 2

Lys Glu Ser Arg Ala Lys Lys Phe Gln Arg Gln His Met Asp Ser Asp
1               5                   10                  15

Ser Ser Pro Ser Ser Ser Ser Thr Tyr Cys Asn Gln Met Met Arg Arg
            20                  25                  30
```

-continued

```
Arg Asn Met Thr Gln Gly Arg Cys Lys Pro Val Asn Thr Phe Val His
        35                  40                  45

Glu Pro Leu Val Asp Val Gln Asn Val Cys Phe Gln Glu Lys Val Thr
    50                  55                  60

Cys Lys Asn Gly Gln Gly Asn Cys Tyr Lys Ser Asn Ser Ser Met His
65                  70                  75                  80

Ile Thr Asp Cys Arg Leu Thr Asn Gly Ser Arg Tyr Pro Asn Cys Ala
                85                  90                  95

Tyr Arg Thr Ser Pro Lys Glu Arg His Ile Ile Val Ala Cys Glu Gly
            100                 105                 110

Ser Pro Tyr Val Pro Val His Phe Asp Ala Ser Val Glu Asp Ser Thr
        115                 120                 125
```

NON-NATURAL RIBONUCLEASE CONJUGATES AS CYTOTOXIC AGENTS

The present Application is a divisional of U.S. patent application Ser. No. 13/923,008, filed Jun. 20, 2013, now U.S. Pat. No. 8,697,065, issued Apr. 15, 2014, which is a divisional of U.S. patent application Ser. No. 11/105,041, filed Apr. 13, 2005, now U.S. Pat. No. 8,470,315, issued Jun. 25, 2013, which claims priority to U.S. Provisional Application Ser. No. 60/561,609 filed Apr. 13, 2004, each of which are herein incorporated by reference.

FIELD OF THE INVENTION

The present invention is directed toward the delivery of a toxic protein to pathogenic cells, particularly cancer cells. In preferred embodiments, the toxic protein is a ribonuclease that has been modified to make it toxic to target cells and that can be conjugated to a target cell-specific delivery vector, such as an antibody, for delivery to pathogenic cells.

BACKGROUND OF THE INVENTION

The term “chemotherapy” simply means the treatment of disease with chemical substances. The father of chemotherapy, Paul Ehrlich, imagined the perfect chemotherapeutic as a “magic bullet;” such a compound would kill invading organisms or cells without harming the host. While significant progress has been made in identifying compounds that kill or inhibit cancer cells and in identifying methods of directing such compounds to the intended target cells, the art remains in need of improved anti-cancer compounds.

SUMMARY OF THE INVENTION

The present invention relates to the use (e.g., therapeutic use, diagnostic use, research use) of proteins to target cancers and other diseases and conditions (e.g., viral or pathogen infections) where selectively killing pathogenic cells is desired. For example, in some embodiments, the present invention relates to the production and delivery of a cytotoxic protein to pathogenic cells such as tumor cells or virus-infected cells. The ribonuclease can also be used to degrade pathogenic RNA outside of the cell. In some preferred embodiments, the present invention provides the use of ribonuclease proteins (e.g., human ribonuclease proteins) that are altered in their amino acid sequence (i.e., non-natural) to make them cytotoxic. In some embodiments, these mutated proteins are specifically delivered to pathogenic cells by conjugation to targeting vectors (e.g., human or humanized protein) that are specific for or at least partially selective for the pathogenic target cells. Such targeting vectors include, but are not limited to, antibodies, receptors, ligands, peptides, nucleic acids, lipids, polymers, small molecules, and synthetic compounds. In some embodiments, mutant ribonuclease genes are delivered as DNA or RNA via expression vectors. The ribonuclease genes may be expressed alone, or may be expressed as chimerical conjugates of the ribonuclease gene with a cell-specific targeting moiety.

The present invention also provides methods comprising the delivery of the cytotoxic ribonucleases under conditions that minimize or eliminate the human immune response against the proteins and delivery vectors. This present invention further provides methods for selective inhibition of cellular growth and/or viral replication in target cells through the action of the mutated ribonucleases.

Thus, in some embodiments, the present invention provides a novel family of proteins for treating, characterizing, or understanding disease. In some embodiments, the compositions of the present invention are used therapeutically, alone or in combination with other compounds or interventions (e.g., to augment existing therapies for treatment of human cancers).

Thus, in some embodiments, the present invention provides a composition comprising a non-natural ribonuclease (e.g., human ribonuclease) conjugated to a cell-specific targeting moiety, wherein the ribonuclease is configured to kill the cell. In some embodiments, the non-natural human ribonuclease comprises a non-natural human ribonuclease one (RNase 1). Examples of suitable non-natural human RNase 1 compounds include, but are not limited to, those having a variant sequence compared to a natural ribonuclease one as shown in Table 1.

TABLE 1

| |
|---|
| N88C |
| L86E, N88R, G89D, R91D |
| R4C, L86E, N88R, G89D, R91D, V118C |
| L86E, N88C, R91D |
| R4C, L86E, N88C, R91D, V118C |
| R4C, N88C, V118C |
| K7A, L86E, N88C, R91D |
| K7A, L86E, N88R, G89D, R91D |
| R4C, K7A, L86E, N88C, R91D, V118C |
| R4C, K7A, L86E, N88R, G89D, R91D, V118C |

The present invention further provides variants of such sequences. Exemplary variants are provided in Tables 2 and 3, below, as well as in Example 2. Additional variants that have the desired function are also within the scope of the invention.

TABLE 2

Human ribonuclease I amino acid modifications for increased cytotoxicity

| Amino Acid Position | Amino Acid Identity | Amino Acids Substitution |
|---|---|---|
| 7 | Lysine (K) | Glycine (G), Alanine (A), Aspartatic acid (D), Glutamatic acid (E), Phenylalanine (F), Tryptophan (W) |
| 85 | Arginine (R) | Aspartatic acid (D), Glutamatic acid (E), Phenylalanine (F), Tryptophan (W), Glycine (G), Alanine (A) |
| 86 | Leucine (L) | Aspartatic acid (D), Glutamatic acid (E), Phenylalanine (F), Lysine (K), Arginine (R), Tryptophan (W) |
| 87 | Threonine (T) | Leucine (L), Phenylalanine (F), Tyrosine (Y), Tryptophan (W) |
| 88 | Asparagine (N) | Lysine (K), Arginine (R), Leucine (L), Aspartic acid (D), Glutamatic acid (E), Phenylalanine (F), Tyrosine (Y), Tryptophan (W) |

TABLE 2-continued

Human ribonuclease I amino acid modifications for increased cytotoxicity

| Amino Acid Position | Amino Acid Identity | Amino Acids Substitution |
|---|---|---|
| 89 | Glycine (G) | Lysine (K), Arginine (R), Leucine (L), Aspartic acid (D), Glutamatic acid (E), Phenylalanine (F), Tyrosine (Y), Tryptophan (W) |
| 90 | Serine (S) | Phenylalanine (F), Tryptophan (W), Aspartatic acid (D), Glutamatic acid (E), Lysine (K), Arginine (R) |
| 91 | Arginine (R) | Aspartatic acid (D), Glutamatic acid (E), Phenylalanine (F), Tryptophan (W) |
| 92 | Tyrosine (Y) | Glycine (G), Alanine (A), Lysine (K), Arginine (R), Aspartic acid (D), Glutamatic acid (E) |
| 93 | Proline (P) | Leucine (L), Phenylalanine (F), Tyrosine (Y), Tryptophan (W), Lysine (K), Arginine (R), Aspartic acid (D), Glutamatic acid (E) |
| 94 | Asparagine (N) | Lysine (K), Arginine (R), Leucine (L), Aspartic acid (D), Glutamatic acid (E), Phenylalanine (F), Tyrosine (Y), Tryptophan (W) |

TABLE 3

| Amino Acid Position | Amino Acid Identity | Amino Acids Substitution |
|---|---|---|
| 1 | Lysine (K) | Cysteine (C) |
| 2 | Glutamic acid (E) | Cysteine (C) |
| 3 | Serine (S) | Cysteine (C) |
| 4 | Arginine (R) | Cysteine (C) |
| 5 | Alanine (A) | Cysteine (C) |
| 6 | Lysine (K) | Cysteine (C) |
| 116 | Valine (V) | Cysteine (C) |
| 117 | Proline (P) | Cysteine (C) |
| 118 | Valine (V) | Cysteine (C) |
| 119 | Histidine (H) | Cysteine (C) |
| 120 | Phenylalanine (F) | Cysteine (C) |
| 121 | Aspartate (D) | Cysteine (C) |

In some embodiments, a plurality of different ribonucleases and/or targeting moieties are provided in a composition (e.g., a kit, a pharmaceutical preparation, etc.)

The present invention is not limited by the nature of or location of the target cell. In some embodiments, the cell is a cancer cell, a cell that expresses a marker associated with viral infection, a cell that is associated with an inflammatory response, and a cell is associated with an autoimmune disease (e.g., a cell expressing markers or otherwise characterized as aberrantly failing to undergo cell death or presenting autoantigens). In some embodiments, the cell resides in vitro (e.g., in culture). In other embodiments, the cell resides in vivo (e.g., in a tissue, as a transplanted cell, in a test animal, in a subject suspected of or diagnosed as having a disease or condition—e.g., cancer).

In some preferred embodiments, the ribonuclease is conjugated to the cell-specific targeting moiety by a linker. The present invention is not limited by the nature of the linker. Linkers suitable for use with the present invention include, but are not limited to, linkers attached to a non-native cysteine of the ribonuclease, non-cleavable linkers, cleavable linker, and linkers attached within a loop region of the ribonuclease corresponding to amino acids 84-95 of bovine ribonuclease A.

In some embodiments, the ribonuclease is made as a fusion protein with a disease-specific protein, such as an antibody or antibody fragment. Those skilled in the art recognize that the fusion can be created using cDNA and standard molecular biology techniques.

The present invention is not limited by the nature of the cell-specific targeting moiety. Targeting moieties include, but are not limited to, immunoglobulins (e.g., antibodies, humanized or partially humanized antibodies, antibody fragments, etc.), proteins, peptides, receptor ligands, aptamers, small molecules, nucleic acid molecules, lipids, etc.

In some embodiments, the components of the composition (e.g., the ribonuclease, the cell specific-targeting moiety) are provided to a cell, alone or together via an expression vector, such that the components are produce within a cell of a subject or produced within a cell provided to the subject (e.g., through ex vivo transfection followed by transplantation).

The present invention further provides methods of killing cell using any of the compositions discussed herein.

DEFINITIONS

Figure 1:
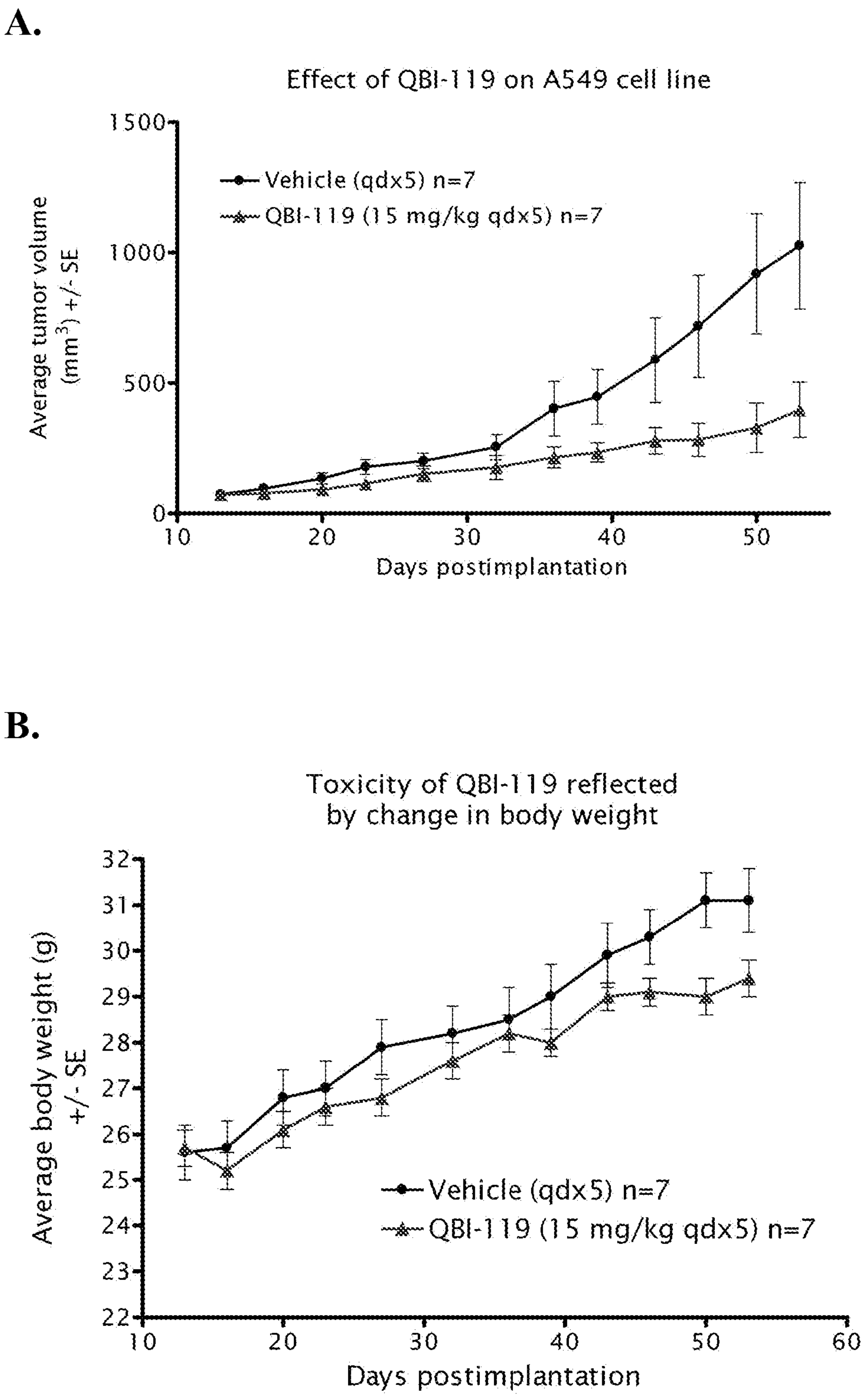
FIG. 1A shows a graph demonstrating the growth inhibiting effect of QBI-119 on tumor volume (A549 cells) over a number of days.
FIG. 1B shows a graph depicting the lack of toxicity of QBI-119.

To facilitate an understanding of the present invention, a number of terms and phrases are defined below:

As used herein, the term "immunoglobulin" or "antibody" refer to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject suspected of having cancer" refers to a subject that presents one or more symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass or increased PSA level) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests (e.g., PSA).

As used herein, the term "subject at risk for cancer" refers to a subject with one or more risk factors for developing a specific cancer. Risk factors include, but are not limited to, gender, age, genetic predisposition, environmental exposure, and previous incidents of cancer, preexisting non-cancer diseases, and lifestyle.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

"Amino acid sequence" and terms such as "polypeptide" or "protein" are not meant to limit the amino acid sequence to the complete, native amino acid sequence associated with the recited protein molecule.

The terms "test compound" and "candidate compound" refer to any chemical or biological entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present invention.

The term "gene" refers to a nucleic acid (e.g., DNA) sequence that comprises coding sequences necessary for the production of a polypeptide or precursor (e.g., ribonucleases or ribonuclease conjugates of the present invention). The polypeptide can be encoded by a full length coding sequence or by any portion of the coding sequence so long as the desired activity or functional properties (e.g., enzymatic activity, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product. This is in contrast to synthetic mutants that are changes made in a sequence through human (or machine) intervention.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

As used herein, the term "purified" or "to purify" refers to the removal of impurities and contaminants from a sample. For example, antibodies are purified by removal of non-immunoglobulin proteins; they are also purified by the removal of immunoglobulin that does not bind an intended target molecule. The removal of non-immunoglobulin proteins and/or the removal of immunoglobulins that do not bind an intended target molecule results in an increase in the percent of target-reactive immunoglobulins in the sample. In another example, recombinant polypeptides are expressed in host cells and the polypeptides are purified by the removal of host cell proteins; the percent of recombinant polypeptides is thereby increased in the sample.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

DETAILED DESCRIPTION OF THE INVENTION

The present invention is directed toward the delivery of a toxic protein to pathogenic cells, particularly cancer cells. The toxic protein may also have benefit when delivered to diseased areas without being toxic to the diseased cells. In preferred embodiments, the toxic protein is a ribonuclease that has been modified to make it toxic to target cells and that can be conjugated to a target cell-specific delivery vector, such as an antibody, for delivery to pathogenic cells.

Preferred embodiments of the present invention are based on the conversion of naturally occurring ribonucleases (e.g., human ribonucleases) into toxic proteins that are used to treat or cure diseases, particularly cancer and viral infections. The compositions also find use in diagnostic applications (e.g., associated with drug screening or cancer characterization) and research applications. These ribonucleases can be used as stand alone reagents or they may be incorporated into general or specific delivery systems such as polymers, dendrimers, liposomes, polymeric nanoparticles, or block copolymer micelles. A feature of these proteins is that they are proteins that have been engineered to be toxic to the cells to which they are delivered. This feature provides a toxin conjugate that is less susceptible to naturally occurring inhibitors of the toxin. Another feature is that their starting point was preferably a natural protein (e.g., a natural human protein) and not a non-natural (e.g., non-human) protein that had to be modified (e.g., humanized) significantly to escape the immune system. One embodiment of this invention is to combine these protein toxins with antibodies (e.g., humanized or human antibodies) for targeting to specific pathogenic cells. These protein conjugates make it much less likely that when used in vivo, they will induce side effects or an immune response.

In some preferred embodiments, the present invention provides conjugates of the EVADE human ribonuclease (Quintessence Biosciences, Madison, Wis.) with a targeting component. As such, the EVADE human ribonucleases exhibit improved efficacy compared to the amphibian ribonucleases because the specific ribonucleolytic activity is higher and the likelihood of side effects and inducing a human immune response is lower. In addition, binding to the native inhibitor, ribonuclease inhibitor, is disrupted for the EVADE ribonucleases. By degrading cellular RNA in target cells, the EVADE ribonucleases inhibit the cellular growth of the tumors and also enhances the anti-cancer effects of conventional therapies, including chemotherapy and radiation. It is also contemplated that EVADE human ribonucleases are not retained in the human kidney, as are amphibian ribonucleases. Renal toxicity of the amphibian ribonucleases is dose limiting in mice and humans. With conventional chemotherapy, it is often a problem that membrane based drug pumps can eliminate the small molecule anti-cancer drugs from the cancerous cell. This requires that higher doses of the toxic drugs be used. Like the amphibian ribonuclease, it is expected that the EVADE ribonucleases are able to make these resistant cells susceptible to standard levels of treatment so that lower doses are effective and side effects reduced. In addition, the EVADE ribonucleases are contemplated to provide benefit when used in combination with radiotherapy or other convention interventions.

In some embodiments, the compositions and methods of the present invention are used to treat diseased cells, tissues, organs, or pathological conditions and/or disease states in a subject organism (e.g., a mammalian subject including, but not limited to, humans and veterinary animals), or in in vitro and/or ex vivo cells, tissues, and organs. In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic.

In some preferred embodiments, the ribonuclease or ribonuclease conjugates of the present invention are co-administered with other medical interventions, either simultaneously or sequentially. For example, for cancer therapy, any oncolytic agent that is routinely used in a cancer therapy may be co-administered with the compositions and methods of the present invention. For example, the U.S. Food and Drug Administration maintains a formulary of oncolytic agents approved for use in the United States. International counterpart agencies to the U.S.F.D.A. maintain similar formularies. Table 4 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents. It is contemplated, that in some cases, co-administration with the compositions of the present invention permits lower doses of such compounds, thereby reducing toxicity.

TABLE 4

| | | |
|---|---|---|
| Aldesleukin (des-alanyl-1, serine-125 human interleukin-2) | PROLEUKIN | Chiron Corp., Emeryville, CA |
| Alemtuzumab (IgG1κ anti CD52 antibody) | CAMPATH | Millennium and ILEX Partners, LP, Cambridge, MA |
| Alitretinoin (9-cis-retinoic acid) | PANRETIN | Ligand Pharmaceuticals, Inc., San Diego CA |
| Allopurinol (1,5-dihydro-4 H-pyrazolo[3,4-d]pyrimidin-4-one monosodium salt) | ZYLOPRIM | GlaxoSmithKline, Research Triangle Park, NC |
| Altretamine (N,N,N',N',N",N",-hexamethyl-1,3,5-triazine-2,4,6-triamine) | HEXALEN | US Bioscience, West Conshohocken, PA |
| Amifostine (ethanethiol, 2-[(3-aminopropyl)amino]-, dihydrogen phosphate (ester)) | ETHYOL | US Bioscience |
| Anastrozole (1,3-Benzenediacetonitrile, a,a,a',a'-tetramethyl-5-(1H-1,2,4-triazol-1-ylmethyl)) | ARIMIDEX | AstraZeneca Pharmaceuticals, LP, Wilmington, DE |
| Arsenic trioxide | TRISENOX | Cell Therapeutic, Inc., Seattle, WA |
| Asparaginase (L-asparagine amidohydrolase, type EC-2) | ELSPAR | Merck & Co., Inc., Whitehouse Station, NJ |
| BCG Live (lyophilized preparation of an attenuated strain of *Mycobacterium bovis* (*Bacillus Calmette*-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | TARGRETIN | Ligand Pharmaceuticals |
| bexarotene gel | TARGRETIN | Ligand Pharmaceuticals |
| Bleomycin (cytotoxic glycopeptide antibiotics produced by *Streptomyces verticillus*; bleomycin $A_2$ and bleomycin $B_2$) | BLENOXANE | Bristol-Myers Squibb Co., NY, NY |
| Capecitabine (5'-deoxy-5-fluoro-N-[(pentyloxy)carbonyl]-cytidine) | XELODA | Roche |
| Carboplatin (platinum, diammine [1,1-cyclobutanedicarboxylato(2-)-0,0']-,(SP-4-2)) | PARAPLATIN | Bristol-Myers Squibb |
| Carmustine (1,3-bis(2-chloroethyl)-1-nitrosourea) | BCNU, BICNU | Bristol-Myers Squibb |
| Carmustine with Polifeprosan 20 Implant | GLIADEL WAFER | Guilford Pharmaceuticals, Inc., Baltimore, MD |

TABLE 4-continued

| | | |
|---|---|---|
| Celecoxib (as 4-[5-(4-methylphenyl)-3-(trifluoromethyl)-1H-pyrazol-1-yl] benzenesulfonamide) | CELEBREX | Searle Pharmaceuticals, England |
| Chlorambucil (4-[bis(2chlorethyl)amino]benzenebutanoic acid) | LEUKERAN | GlaxoSmithKline |
| Cisplatin ($PtCl_2H_6N_2$) | PLATINOL | Bristol-Myers Squibb |
| Cladribine (2-chloro-2'-deoxy-b-D-adenosine) | LEUSTATIN, 2-CDA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | CYTOXAN, NEOSAR | Bristol-Myers Squibb |
| Cytarabine (1-b-D-Arabinofuranosylcytosine, $C_9H_{13}N_3O_5$) | CYTOSAR-U | Pharmacia & Upjohn Company |
| cytarabine liposomal | DEPOCYT | Skye Pharmaceuticals, Inc., San Diego, CA |
| Dacarbazine (5-(3,3-dimethyl-1-triazeno)-imidazole-4-carboxamide (DTIC)) | DTIC-DOME | Bayer AG, Leverkusen, Germany |
| Dactinomycin, actinomycin D (actinomycin produced by *Streptomyces parvullus*, $C_{62}H_{86}N_{12}O_{16}$) | COSMEGEN | Merck |
| Darbepoetin alfa (recombinant peptide) | ARANESP | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DANUOXOME | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | CERUBIDINE | Wyeth Ayerst, Madison, NJ |
| Denileukin diftitox (recombinant peptide) | ONTAK | Seragen, Inc., Hopkinton, MA |
| Dexrazoxane ((S)-4,4'-(1-methyl-1,2-ethanediyl)bis-2,6-piperazinedione) | ZINECARD | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | TAXOTERE | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | ADRIAMYCIN, RUBEX | Pharmacia & Upjohn Company |
| doxorubicin | ADRIAMYCIN PFS INTRAVENOUS INJECTION | Pharmacia & Upjohn Company |
| doxorubicin liposomal | DOXIL | Sequus Pharmaceuticals, Inc., Menlo park, CA |
| dromostanolone propionate (17b-Hydroxy-2a-methyl-5a-androstan-3-one propionate) | DROMOSTANOLONE | Eli Lilly & Company, Indianapolis, IN |
| dromostanolone propionate | MASTERONE INJECTION | Syntex, Corp., Palo Alto, CA |
| Elliott's B Solution | ELLIOTT'S B SOLUTION | Orphan Medical, Inc |
| Epirubicin ((8S-cis)-10-[(3-amino-2,3,6-trideoxy-a-L-arabin-hexopyranosyl)oxy]-7,8,9,10-tetrahydro-6,8,11-trihydroxy-8-(hydroxyacetyl)-1-methoxy-5,12-naphthacenedione hydrochloride) | ELLENCE | Pharmacia & Upjohn Company |
| Epoetin alfa (recombinant peptide) | EPOGEN | Amgen, Inc |

TABLE 4-continued

| | | |
|---|---|---|
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | EMCYT | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | ETOPOPHOS | Bristol-Myers Squibb |
| etoposide, VP-16 (4'-demethylepipodophyllotoxin 9-[4,6-0-(R)-ethylidene-(beta)-D-glucopyranoside]) | VEPESID | Bristol-Myers Squibb |
| Exemestane (6-methylenandrosta-1,4-diene-3,17-dione) | AROMASIN | Pharmacia & Upjohn Company |
| Filgrastim (r-metHuG-CSF) | NEUPOGEN | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | FLUDARA | Berlex Laboratories, Inc., Cedar Knolls, NJ |
| Fluorouracil, 5-FU (5-fluoro-2,4(1H,3H)-pyrimidinedione) | ADRUCIL | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | FASLODEX | IPR Pharmaceuticals, Guayama, Puerto Rico |
| Gemcitabine (2'-deoxy-2',2'-difluorocytidine monohydrochloride (b-isomer)) | GEMZAR | Eli Lilly |
| Gemtuzumab Ozogamicin (anti-CD33 hP67.6) | MYLOTARG | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | ZOLADEX IMPLANT | AstraZeneca Pharmaceuticals |
| Hydroxyurea | HYDREA | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | ZEVALIN | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | IDAMYCIN | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | GLEEVEC | Novartis AG, Basel, Switzerland |
| Interferon alfa-2a (recombinant peptide) | ROFERON-A | Hoffmann-La Roche, Inc., Nutley, NJ |
| Interferon alfa-2b (recombinant peptide) | INTRON A (LYOPHILIZED BETASERON) | Schering AG, Berlin, Germany |
| Irinotecan HCl ((4S)-4,11-diethyl-4-hydroxy-9-[(4-piperidinopiperidino)carbonyloxy]-1H-pyrano[3',4':6,7] indolizino[1,2-b] quinoline-3,14(4H,12H) dione hydrochloride trihydrate) | CAMPTOSAR | Pharmacia & Upjohn Company |
| Letrozole (4,4'-(1H-1,2,4-Triazol-1-ylmethylene) dibenzonitrile) | FEMARA | Novartis |
| Leucovorin | WELLCOVORIN, | Immunex, Corp., |

TABLE 4-continued

| | | |
|---|---|---|
| (L-Glutamic acid, N[4[[(2amino-5-formyl-1,4,5,6,7,8 hexahydro4oxo6-pteridinyl)methyl]amino]benzoyl], calcium salt (1:1)) | LEUCOVORIN | Seattle, WA |
| Levamisole HCl ((−)-(S)-2,3,5,6-tetrahydro-6-phenylimidazo [2,1-b] thiazole monohydrochloride $C_{11}H_{12}N_2S$•HCl) | ERGAMISOL | Janssen Research Foundation, Titusville, NJ |
| Lomustine (1-(2-chloro-ethyl)-3-cyclohexyl-1-nitrosourea) | CEENU | Bristol-Myers Squibb |
| Meclorethamine, nitrogen mustard (2-chloro-N-(2-chloroethyl)-N-methylethanamine hydrochloride) | MUSTARGEN | Merck |
| Megestrol acetate 17α(acetyloxy)-6-methylpregna-4,6-diene-3,20-dione | MEGACE | Bristol-Myers Squibb |
| Melphalan, L-PAM (4-[bis(2-chloroethyl) amino]-L-phenylalanine) | ALKERAN | GlaxoSmithKline |
| Mercaptopurine, 6-MP (1,7-dihydro-6H-purine-6-thione monohydrate) | PURINETHOL | GlaxoSmithKline |
| Mesna (sodium 2-mercaptoethane sulfonate) | MESNEX | Asta Medica |
| Methotrexate (N-[4-[[(2,4-diamino-6-pteridinyl)methyl]methylamino]benzoyl]-L-glutamic acid) | METHOTREXATE | Lederle Laboratories |
| Methoxsalen (9-methoxy-7H-furo[3,2-g][1]-benzopyran-7-one) | UVADEX | Therakos, Inc., Way Exton, Pa |
| Mitomycin C | MUTAMYCIN | Bristol-Myers Squibb |
| mitomycin C | MITOZYTREX | SuperGen, Inc., Dublin, CA |
| Mitotane (1,1-dichloro-2-(o-chlorophenyl)-2-(p-chlorophenyl) ethane) | LYSODREN | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | NOVANTRONE | Immunex Corporation |
| Nandrolone phenpropionate | DURABOLIN-50 | Organon, Inc., West Orange, NJ |
| Nofetumomab | VERLUMA | Boehringer Ingelheim Pharma KG, Germany |
| Oprelvekin (IL-11) | NEUMEGA | Genetics Institute, Inc., Alexandria, VA |
| Oxaliplatin (cis-[(1R,2R)-1,2-cyclohexanediamine-N,N'] [oxalato(2-)-O,O'] platinum) | ELOXATIN | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | AREDIA | Novartis |
| Pegademase ((monomethoxypolyethylene glycol succinimidyl) 11-17-adenosine deaminase) | ADAGEN (PEGADEMASE BOVINE) | Enzon Pharmaceuticals, Inc., Bridgewater, NJ |
| Pegaspargase (monomethoxypolyethylene glycol succinimidyl L-asparaginase) | ONCASPAR | Enzon |
| Pegfilgrastim (covalent conjugate of recombinant methionyl human G-CSF (Filgrastim) and monomethoxypolyethylene glycol) | NEULASTA | Amgen, Inc |
| Pentostatin | NIPENT | Parke-Davis Pharmaceutical Co., Rockville, MD |
| Pipobroman | VERCYTE | Abbott Laboratories, Abbott Park, IL |
| Plicamycin, Mithramycin (antibiotic produced by *Streptomyces plicatus*) | MITHRACIN | Pfizer, Inc., NY, NY |

TABLE 4-continued

| | | |
|---|---|---|
| Porfimer sodium | PHOTOFRIN | QLT Phototherapeutics, Inc., Vancouver, Canada |
| Procarbazine (N-isopropyl-1-μ-(2-methylhydrazino)-p-toluamide monohydrochloride) | MATULANE | Sigma Tau Pharmaceuticals, Inc., Gaithersburg, MD |
| Quinacrine (6-chloro-9-(1-methyl-4-diethyl-amine) butylamino-2-methoxyacridine) | ATABRINE | Abbott Labs |
| Rasburicase (recombinant peptide) | ELITEK | Sanofi-Synthelabo, Inc., |
| Rituximab (recombinant anti-CD20 antibody) | RITUXAN | Genentech, Inc., South San Francisco, CA |
| Sargramostim (recombinant peptide) | PROKINE | Immunex Corp |
| Streptozocin (streptozocin 2-deoxy-2-[[(methylnitrosoamino)carbonyl]amino]-a(and b)-D-glucopyranose and 220 mg citric acid anhydrous) | ZANOSAR | Pharmacia & Upjohn Company |
| Talc ($Mg_3Si_4O_{10}(OH)_2$) | SCLEROSOL | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | NOLVADEX | AstraZeneca Pharmaceuticals |
| Temozolomide (3,4-dihydro-3-methyl-4-oxoimidazo[5,1-d]-as-tetrazine-8-carboxamide) | TEMODAR | Schering |
| teniposide, VM-26 (4'-demethylepipodophyllotoxin 9-[4,6-0-(R)-2-thenylidene-(beta)-D-glucopyranoside]) | VUMON | Bristol-Myers Squibb |
| Testolactone (13-hydroxy-3-oxo-13,17-secoandrosta-1,4-dien-17-oic acid [dgr]-lactone) | TESLAC | Bristol-Myers Squibb |
| Thioguanine, 6-TG (2-amino-1,7-dihydro-6H-purine-6-thione) | THIOGUANINE | GlaxoSmithKline |
| Thiotepa (Aziridine, 1,1',1''-phosphinothioylidynetris-, or Tris (1-aziridinyl) phosphine sulfide) | THIOPLEX | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | HYCAMTIN | GlaxoSmithKline |
| Toremifene (2-(p-[(Z)-4-chloro-1,2-diphenyl-1-butenyl]-phenoxy)-N,N-dimethylethylamine citrate (1:1)) | FARESTON | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | BEXXAR | Corixa Corp., Seattle, WA |
| Trastuzumab (recombinant monoclonal $IgG_1$ kappa anti-HER2 antibody) | HERCEPTIN | Genentech, Inc |
| Tretinoin, ATRA (all-trans retinoic acid) | VESANOID | Roche |
| Uracil Mustard | URACIL MUSTARD CAPSULES | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | VALSTAR | Anthra --> Medeva |
| Vinblastine, Leurocristine ($C_{46}H_{56}N_4O_{10}$•$H_2SO_4$) | VELBAN | Eli Lilly |
| Vincristine ($C_{46}H_{56}N_4O_{10}$•$H_2SO_4$) | ONCOVIN | Eli Lilly |

TABLE 4-continued

| | | |
|---|---|---|
| Vinorelbine (3',4'-didehydro-4'-deoxy-C'-norvincaleukoblastine [R-(R*,R*)-2,3-dihydroxybutanedioate (1:2)(salt)]) | NAVELBINE | GlaxoSmithKline |
| Zoledronate, Zoledronic acid ((1-Hydroxy-2-imidazol-1-yl-phosphonoethyl) phosphonic acid monohydrate) | ZOMETA | Novartis |

A current and still developing approach to cancer therapy involves using cancer cell-specific reagents to target a malignant tumor. These toxic reagents can be produced by attaching a toxic payload to a cell-specific delivery vector. Over the past few years, a wide variety of tumor-specific targeting proteins, including antibodies, antibody fragments, and ligands for cell surface receptors have been developed and clinically tested. These targeting molecules have been conjugated to several classes of therapeutic toxins such as small molecule drugs, enzymes, radioisotopes, protein toxins, and other toxins for specific delivery to patients. While these efforts have made meaningful inroads to treat cancers, significant challenges lie ahead to develop more effective toxins, to create more robust and specific delivery systems, and to design therapeutic proteins and protein vectors that evade immune surveillance in humans.

Ribonuclease (RNase) proteins have been tested as human therapeutics because they selectively target tumor cells; this has been demonstrated most clearly with an RNase from *Rana pipiens* early embryos. *Rana pipiens* is a species of leopard frogs and its embryonic RNase is distantly related to the more highly conserved bovine and human pancreatic ribonucleases. In mammalian cells, pancreatic-type ribonucleases, such as RNase A, are secretory enzymes that catalyze the degradation of RNA to ribonucleotides and their activity is inhibited by binding to ribonuclease inhibitor (RI), a ubiquitous cytosolic protein. Ribonuclease inhibitor binds exceptionally tight to pancreatic-type RNases, abating their activity and thereby making them non-toxic to normal or cancer cells. If the RNase activity is inhibited, the cellular RNA is undamaged and the cell remains viable. In normal cells the ribonuclease activity is tightly controlled, but if ribonuclease activity is uncontrolled, the ribonucleolytic activity destroys cellular RNA and kills the cell. There are two main approaches to making a ribonuclease toxic to human cells, especially cancer cells. The first approach is to select a ribonuclease that is evolutionarily distant to humans and is not inhibited by human ribonuclease inhibitor protein. The frog (*Rana pipiens*) ribonuclease, when placed in a human cell, is not strongly inhibited by RI and its RNase activity destroys cellular RNA and kills the target cell. This has been the approach with a specific *Rana pipiens* RNase called Ranpirnase. Ranpirnase is generic name of the pharmaceutical that is described and claimed in U.S. Pat. No. 5,559,212 and that is presently known by the registered trademark ONCONASE.

The second approach is to mutate mammalian ribonucleases so that they maintain high levels of ribonucleolytic activity but are not significantly inhibited by human ribonuclease inhibitor. These mutated enzymes provide high levels of ribonucleolytic activity within cancer cells because of disruption of binding to RI. This unregulated activity is particularly lethal to cancer cells. This mutation approach has been demonstrated with the mammalian proteins bovine RNase A and human RNase I and is described in U.S. Pat. Nos. 5,389,537 and 6,280,991, the disclosures of which are herein incorporated by reference in their entireties.

An ideal protein candidate for cancer therapy would be more toxic to tumor cells compared to non-cancerous cells and would be targetable to a specific tumor. This candidate should have few side effects and should not stimulate a human immune response. Therapeutic proteins that elicit immune responses in humans are always problematic and often unacceptable. The present invention provides ribonuclease conjugates that are derived from mutated RNases that exhibit low immunogenicity and side effects and still maintain high ribonucleolytic activity resulting in cancer-specific toxicity.

Certain preferred embodiments of the present invention are described below. While these embodiments are illustrated with variant human ribonuclease proteins and antibody targeting moieties, the present invention is not so limited.

Therapeutic Antibodies and Delivery of Cytotoxins

Antibodies are glycoprotein molecules produced by white blood cells (B-lymphocytes) of the immune system and their function is to recognize and bind to matter harmful to the organism. Once an antigen is marked by an antibody, it is destroyed by other components of the immune system. A typical organism makes millions of different antibodies, each designed to bind a specific epitope (or antigenic determinant) on the foreign antigen. Antibodies naturally combine specificity (the ability to exquisitely discriminate diverse harmful molecules) and affinity (the ability to tightly lock onto those targets) with the ability to recruit effector functions of the immune system such as antibody- and complement-mediated cytolysis and antibody-dependent cell-mediated cytotoxicity (ADCC). Many new therapeutic approaches involving antibodies have succeeded in potentiating the natural antibody functions to treat or cure diseases.

Alternatively, a "toxic payload" (such as a radioactive element or a toxin) attached to the antibody can be accurately delivered to the pathogenic target. The following table lists the mechanisms of some cancer therapeutic antibodies, including three antibody conjugates that carry a toxic payload for lymphomas and leukemias. (Drug Discovery Today, Vol. 8, No. 11 Jun. 2003). Two of the conjugates, ZEVALIN and BEXXAR, carry radioactive iodine as the toxin and the third, MYLOTARG, carries a cytotoxic antitumor antibiotic, calicheaminin which is isolated from a bacterial fermentation. The Mylotarg antibody binds specifically to the CD33 antigen which is expressed on the surface of leukemic blasts that are found in more than 80% of patients with acute myeloid leukemia (AML). The antibody in this conjugate has approximately 98.3% of its amino acid sequences derived from human origins.

TABLE 2

| Antibody Mode of Action | Product | Antibody Target |
|---|---|---|
| Blockade Ligand binding | ERBITUX | EGF receptor |
| | HUMAX-EGFR | EGF receptor |
| Complement Dependent Cytotoxicity | RITUXAN | CD20 |
| | HUMAX-CD20 | CD20 |
| | CAMPATH-1H | CD52 |
| Antibody dependent cell-mediated cytotoxicity | RIXTUXAN | CD20 |
| | HUMAX-CD20 | CD20 |
| | HERCEPTIN | Her-2/neu |
| | HUMAX-EGFR | EGF receptor |
| Apoptosis induction | Various | IdiotypeB cell tumors |
| Disruption signaling | 2C4 (PERTUZUMAB) | Her-2/neu |
| Inhibition angiogenesis | AVASTIN | VEGF |
| Targeted radiolysis conjugate | ZEVALIN | CD20 |
| | BEXXAR | CD20 |
| Toxin-mediated killing by conjugate | MYLOTARG | CD33 |
| Antagonist activity | MDX-010 | CTLA4 |
| Agonist activity | Various | CD40, CD137 |
| Antagonist activity | Preclinical MAb | Epithelial cell receptor protein tyrosine kinase (EphA2) |
| Antagonist activity | Phase II MAb | alpha 5 beta 3 integrin (receptor) |
| Antagonist activity | Phase I bispecific single chain monoclonal antibody | CD19/CD3 |
| Antagonist activity | Preclinical MAb | Interleukin 9 |
| Antagonist activity | RespiGam Polyclonal Antibody | Respiratory syncytial virus |
| Antagonist activity | Phase II MAb | CD2 |
| Catalytic Activity | MAb | Cocaine cleavage |
| Anti-infective, bacteria | MAb | bacteria |
| Immunosuppressive Agents | MAb | Graft versus Host Disease |
| Anti-infective, virus | MAb | Human metapneumovirus |
| Cytostatic agent | MAb | Platelet derived growth factor |
| Cancer growth and metastosis | Preclinical MAb | Human beta hydroxylases |
| Treatment of autoimmune disease | MAb Medi 507 | Mixed lymphocyte responses |
| Anti-infective, virus | Polyclonal antibody | cytomegalovirus |
| Anti-idiotype antibody | MAb | Neu-glycolyl-GM3 ganglioside |
| Prodrug carrier | MAb | Immungen's CC 1065 prodrugs |
| Toxin-mediated killing by conjugate | Preclinical MAb and taxane derivatives | Various by Immunogen |
| Toxin-mediated killing by conjugate | Cantuzumab mertansine conjugate | Can Ag receptor by immunogen |
| Toxin-mediated killing by conjugate | Phase II MAb maytansinoid conjugate | CD56 |
| Toxin for mitosis inhibition | MAb maitansine conjugate | various |
| Toxin-mediated killing by conjugate | Preclinical MAb cytotoxic drug DM1 conjugate | Antigen on squamous cell cancer (Immunogen) |

Any of the targeting antibodies or agents used in these products may also be employed by the compositions and methods of the present invention.

Generally, the most specific method for targeting toxins is the use of monoclonal antibodies or antibody fragments that are designed to recognize surface antigens specific to tumor cells. Because normal cells lack the surface antigens, they are not targeted and killed by the toxin conjugate. Whole antibodies have two domains: a variable domain that gives the antibody its affinity and binding specificity and a constant domain that interacts with other portions of the immune system to stimulate immune responses in the host organism. The variable domain is composed of the complementarity determining regions (CDRs), which bind to the antibody's target, and a framework region that anchors the CDRs to the rest of the antibody and helps maintain CDR shape. The six CDR's in each antibody differ in length and sequence between different antibodies and are mainly responsible for the specificity (recognition) and affinity (binding) of the antibodies to their target markers.

The functions of antibodies are reflected in their characteristic three-dimensional structure, which is ultimately determined by the primary sequence of amino acids and how those amino acids fold into a functional 3-dimensional protein chain. A step in developing therapeutic monoclonal antibodies is to simultaneously optimize biochemical and cellular functions for anti-cancer performance and still keep the protein as humanlike as possible to minimize any anti-antibody human immune response.

Monoclonal antibodies were originally produced in mice, but when they are used in human therapeutic applications, they present formidable obstacles. Mouse antibodies are recognized as foreign by the human immune system and thus they provoke the Human Anti-Mouse Antibody or HAMA reaction. The HAMA reaction alters the mouse monoclonal effectiveness and can cause severe adverse symptoms in the recipient. Furthermore, mouse antibodies are simply not as effective as human antibodies in mediating the human immune system to destroy the malignant cells. For these reasons, it is often desired to design monoclonal antibodies that are as humanlike as possible but still maintain optimal biochemical, immunological, and therapeutic performance.

There are several factors that influence whether a therapeutic antibody will induce an immune response in the human host. These include the efficiency of uptake by an APC (antigen presenting cell) via pinocytosis, receptor-mediated endocytosis, or phagocytosis. The efficiency of uptake is in turn influenced by the route of administration, the solubility (or aggregation) of the protein, its receptor binding specificity, and whether the protein is recognized by class II major histocompatibility complex (MHC) molecules, T-cell receptors (TCR), and B-cell receptors (BCR). One of the most straightforward ways to evade the human immune response is to make the therapeutic protein sequence and structure as humanlike as possible.

Two main approaches have emerged to produce human or humanized therapeutic monoclonal antibodies, either used alone as a therapeutic or as a carrier for a toxin. These include 1) 'humanizing' mouse or other non-human antibodies to make them compatible with the human immune system and 2) producing fully human antibodies in transgenic mice or by using genetic engineering methods in the laboratory. The processes have produced several categories of monoclonal antibodies. These include mouse, chimaeric, humanized and human antibodies. They are described briefly below:

1. Murine Monoclonal antibodies from mice and rats: The original Kohler and Milstein technology from 1975 provided mouse monoclonal antibodies using a hybridoma technology. These have been used therapeutically. In 1986, the first approved use of mouse monoclonals was for transplant patients whose immune system was suppressed to avoid organ rejection. Rodent antibodies tend to provoke strong Human anti-Murine Antibody (HAMA) immune responses that restrict their usefulness for repeated application in the same patient.
2. Chimaeric Antibodies: These are mutated antibodies in which the entire variable regions of a functional mouse antibody are joined to human constant regions. These antibodies have human effector functions from the constant (Fc regions) such as activating complement and recruiting immune cells. These chimaeric antibodies also reduce the immunogenicity (HAMA) caused by the mouse constant region.
3. Humanized/CDR grafted/Reshaped antibodies: These antibodies are more humanlike than chimaeric antibodies because only the complementarity determining regions from the mouse antibody variable regions are combined with framework regions from human variable regions. Because these antibodies are more human-like than chimaeric antibodies, it is expected they could be designed to be less immunogenic when given to human in recurring therapeutic doses. Using computer modeling software to guide the humanization of murine antibodies or random shuffling of sequences followed by screening, it is possible to design an antibody that retains most or all of the binding affinity and specificity of the murine antibody but which is >90% human.
4. Human antibodies from immune donors: Some antibodies have been rescued from immune human donors using either Epstein Barr Virus transformation of B-cells or by PCR cloning and phage display. By definition these antibodies are completely human in origin.
5. Fully human antibodies from phage libraries: Synthetic phage libraries have been created which use randomized combinations of synthetic human antibody V-regions. By panning these libraries against a target antigen, these so called 'fully human antibodies' are assumed to be very human but possibly more diverse than natural antibodies.
6. Fully human antibodies from transgenic mice: Transgenic mice have been created that have functional human immunoglobulin germline genes sequences. These transgenic mice produce human-like antibodies when immunized.

The human antibodies produced by methods 4, 5, and 6 are typically most desired because they produce a starting antibody that contains no mouse or otherwise "foreign" protein sequences that should stimulate an immune response in human patient. This approach (in 4, 5, and 6) also can bypass the challenge of substituting mouse CDR regions into human frameworks that often alters the 3-dimensional structure of the variable region, thereby changing the antibody's binding and specificity. This approach (in 4, 5, 6) successfully produced an anti-CD3 antibody. The murine version elicited neutralizing antibodies after a single dose in all patients tested, while a humanized version was only immunogenic in 25% of patients following multiple injections.

Besides making monoclonal antibodies as human-like as possible in the primary sequence to escape the human immune response, several other approaches make antibodies less immunogenic and more therapeutically effective are available. One approach is to covalently modify the antibody surface with reagents such as polyethylene glycol (PEG) to suppress its antigenicity and improve its solubility. These biochemical modifications also can have several other benefits such as reduced toxicity, increased bioavailability, and improved efficacy. Another approach is to use antibody fragments in which the potentially antigenic parts of the mouse antibody, such as the constant region, have been removed. This approach typically works only when the regulatory components within the antibody constant region are not required for therapeutic efficacy. Neither of these approaches has proven completely satisfactory, which has driven the humanization effort to produce 'the ideal' antibody candidate mentioned above.

In addition to antibody delivery vectors, toxic molecules can be delivered to cancer cells using several other specific and non-specific vectors including peptides, polymers, dendrimers, liposomes, polymeric nanoparticles, and block copolymer micelles. For example, peptides that bind to the leutinizing hormone-releasing hormone have been used to target a small molecule toxin, camptothecin, to ovarian cancer cells (Journal of Controlled Release, 2003, 91, 61-73).

Ribonucleases that evade ribonuclease inhibitor protein are effective toxins in human cells, particularly against cancer cells. The following references, each of which is herein incorporated by reference in its entirety, describe some chemical conjugates of ribonucleases to targeting proteins (including proteins and antibodies): Newton et al. (2001), Blood 97(2): 528-35, Hursey et al. (2002) Leuk Lymphoma 43(5): 953-9, Rybak et al., (1991) Journal of Biological Chemistry 266(31): 21202-7, Newton et al. (1992) Journal of Biological Chemistry 267(27): 19572-8, Jinno and Ueda (1996) Cancer Chemother Pharmacol 38: 303-308, Yamamura et al. (2002) Eur J Surg 168: 49-54, Jinno et al. (1996) Life Sci 58: 1901-1908, Suzuki et al. (1999) Nature Biotechnology 17(3): 265-70, Rybak et al. (1992), Cell Biophys 21(1-3): 121-38, Jinno et al. (2002) Anticancer Res. 22: 4141-4146.

Non-Natural Ribonuclease Polynucleotides

As described above, a new family of non-natural ribonuclease proteins that have been discovered. This family was identified by structure-function analysis for ribonuclease sequence with desired cytotoxic activities. Accordingly, the present invention provides nucleic acids encoding these novel non-natural ribonucleases, homologs, and variants (e.g., mutations and polyporphisms). In some embodiments, the present invention provides polynucleotide sequences encoding any of the amino acid sequences listed in Tables 1-3. The present invention also provides nucleic acid that are capable of hybridizing to such nucleic acid sequences under conditions of low to high stringency as long as the polynucleotide sequence capable of hybridizing encodes a protein that retains a biological activity of a ribonuclease (e.g., cytotoxic activity). The above nucleic acid molecules may also be associated with coding sequences of targeting molecules (e.g., antibodies) such that the produced amino acid sequence is a fusion between the ribonuclease and the targeting molecule.

In still other embodiments of the present invention, the nucleotide sequences of the present invention may be engineered in order to alter a ribonuclease coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to change codon preference, etc.).

It is contemplated that it is possible to modify the structure of a peptide having a function (e.g., ribonuclease function) for such purposes as increasing activity of the ribonuclease (e.g., cytotoxic activity). Such modified peptides are considered functional equivalents of peptides having an activity of a ribonuclease as defined herein. A modified peptide can be produced in which the nucleotide sequence encoding the polypeptide has been altered, such as by substitution, deletion, or addition. In particularly preferred embodiments, these modifications do not significantly reduce the cytotoxic activity of the modified ribonuclease. In other words, construct "X" can be evaluated in order to determine whether it is a member of the genus of modified or variant ribonucleases of the present invention as defined functionally, rather than structurally. In preferred embodiments, the activity of a variant ribonuclease is evaluated by any known screening method, including those described herein expressly or by reference.

Moreover, variant forms of ribonucleases, as shown in Tables 2 and 3, are provided. Further variations of these compositions are contemplated, including structural and functional equivalents. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ribonucleases disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, $2^{nd}$ ed, WH Freeman and Co., 1981). Whether a change in the amino acid sequence of a peptide results in a functional homolog can be readily determined by assessing the ability of the variant peptide to function in a fashion similar to the reference protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants. In still other embodiments of the present invention, the nucleotide sequences of the present invention may be engineered in order to alter a ribonuclease coding sequence including, but not limited to, alterations that modify the cloning, processing, localization, secretion, and/or expression of the gene product.

Non-Natural Ribonuclease Polypeptides

Non-natural ribonuclease polypeptides are described in Tables 1-3. The present invention also provides fragments, fusion proteins or functional equivalents of these ribonuclease proteins.

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above. In some embodiments of the present invention, the constructs comprise a vector, such as a plasmid or viral vector, into which a sequence of the invention has been inserted, in a forward or reverse orientation. In still other embodiments, the heterologous structural sequence is assembled in appropriate phase with translation initiation and termination sequences. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin by 100 to 270, a cytomegalovirus early promoter enhancer, the polyoma enhancer on the late side of the replication origin, and adenovirus enhancers.

In other embodiments, the expression vector also contains a ribosome-binding site for translation initiation and a transcription terminator. In still other embodiments of the present invention, the vector may also include appropriate sequences for amplifying expression.

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

The polypeptides of the present invention may also be chemically synthesized (Gutte, B. and Merrifield, R. B. The synthesis of ribonuclease A. *J. Biol. Chem.* 1971, 2461, 1722-1741).

The present invention further contemplates methods of generating sets of combinatorial mutants of the present ribonuclease proteins and ribonuclease conjugates. Library are screened to generate, for example, novel ribonuclease or ribonuclease conjugate variants with improved properties (e.g., cytotoxicity against target cells, cell targeting, low systemic toxicity, stability, clearance, and improved storage, handling, and administration).

In some embodiments of the combinatorial mutagenesis approach of the present invention, the amino acid sequences for a population of ribonuclease variants or other related proteins are aligned, preferably to promote the highest homology possible. Such a population of variants can include, for example, ribonuclease homologs from one or more species, or ribonuclease variants from the same species but which differ due to mutation. Amino acids that appear at each position of the aligned sequences are selected to create a degenerate set of combinatorial sequences.

In a preferred embodiment of the present invention, the combinatorial ribonuclease library is produced by way of a degenerate library of genes encoding a library of polypeptides which each include at least a portion of potential ribonuclease protein sequences. For example, a mixture of synthetic oligonucleotides can be enzymatically ligated into gene sequences such that the degenerate set of potential ribonuclease sequences are expressible as individual polypeptides, or alternatively, as a set of larger fusion proteins (e.g., for phage display) containing the set of ribonuclease sequences therein.

There are many ways by which the library of potential ribonuclease homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ribonuclease sequences. The synthesis of degenerate oligonucleotides is well known in the art (See e.g., Narang, Tetrahedron Lett., 39:3 9 [1983]; Itakura et al., Recombinant DNA, in Walton (ed.), Proceedings of the 3rd Cleveland Symposium on Macromolecules, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386-390 [1980]; Roberts et al., Proc. Natl. Acad. Sci. USA 89:2429-2433 [1992]; Devlin et al., Science 249: 404-406 [1990]; Cwirla et al., Proc. Natl. Acad. Sci. USA 87: 6378-6382 [1990]; as well as U.S. Pat. Nos. 5,223,409, 5,198, 346, and 5,096,815, each of which is incorporated herein by reference).

It is contemplated that the ribonuclease nucleic acids can be utilized as starting nucleic acids for directed evolution. These techniques can be utilized to develop ribonuclease variants having desirable properties.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458-67 [1996]; Leung et al., Technique, 1:11-15 [1989]; Eckert and Kunkel, PCR Methods Appl., 1:17-24 [1991]; Caldwell and Joyce, PCR Methods Appl., 2:28-33 (1992); and Zhao and Arnold, Nuc. Acids. Res., 25:1307-08 [1997]). After mutagenesis, the resulting clones are selected for desirable activity (e.g., screened for ribonuclease activity and/or cytotoxicity). Successive rounds of mutagenesis and selection are often necessary to develop enzymes with desirable properties. It should be noted that, preferably, only the useful mutations are carried over to the next round of mutagenesis.

In other embodiments of the present invention, the polynucleotides of the present invention are used in gene shuffling or sexual PCR procedures (e.g., Smith, Nature, 370:324-25 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398-91 [1994]; Stemmer, Proc. Natl. Acad. Sci. USA, 91, 10747-51 [1994]; Crameri et al., Nat. Biotech., 14:315-19 [1996]; Zhang et al., Proc. Natl. Acad. Sci. USA, 94:4504-09 [1997]; and Crameri et al., Nat. Biotech., 15:436-38 [1997]).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of ribonuclease homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

EXAMPLES

Example 1

Exemplary Embodiments

The following Example describes a number of exemplary embodiments of the compositions and methods of the present invention.

Ribonuclease:

The EVADE family of ribonucleases comprises several members, based on human ribonuclease one (RNase I, also known as human pancreatic ribonuclease, hpRNase or hRNase). Some of the EVADE ribonucleases have been assigned the following numbers (QBI-#####) and the single letters and numbers describe the amino acid changes. For example, N88C refers to a substitution of Cysteine (C) for Asparagine (N) at position 88.

Amino acid sequence for bovine ribonuclease A

| | | | |
|---|---|---|---|
| 1<br>KETAAAKFE | 10<br>RQHMDSSTSA | 20<br>ASSSNYCNQM | 30<br>MKSRNLTKDR |
| 40<br>CKPVNTFVHE | 50<br>SLADVQAVCS | 60<br>QKNVACKNGQ | 70<br>TNCYQSYSTM |
| 80<br>SITDCRETGS | 90<br>SKYPNCAYKT | 100<br>TQANKHIIVA | 110<br>CEGNPYVPVH |
| 120<br>FDASV | | | |

Amino acid sequence for human pancreatic ribonuclease I

| | | | |
|---|---|---|---|
| 1<br>KESRAKKFQ | 10<br>RQHMDSDSSP | 20<br>SSSSTYCNQM | 30<br>MRRRNMTQGR |
| 40<br>CKPVNTFVHE | 50<br>PLVDVQNVCF | 60<br>QEKVTCKNGQ | 70<br>GNCYKSNSSM |
| 80<br>HITDCRLTNG | 90<br>SRYPNCAYRT | 100<br>SPKERHIIVA | 110<br>CEGSPYVPVH |
| 120<br>FDASVEDST | | | |

| Amino Acid | Three Letter Abbreviations | Single Letter Abbreviations |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |

-continued

| Amino Acid | Three Letter Abbreviations | Single Letter Abbreviations |
|---|---|---|
| Tyrosine | Tyr | Y |
| Valine | Val | V |

| | |
|---|---|
| QBI-50101 | N88C RNase I |
| QBI-50109 | L86E, N88R, G89D, R91D RNase I |
| QBI-50110 | R4C, L86E, N88R, G89D, R91D, V118C RNase I |
| QBI-50111 | L86E, N88C, R91D RNase I |
| QBI-50112 | R4C, L86E, N88C, R91D, V118C RNase I |
| QBI-50118 | R4C, N88C, V118C RNase I |
| QBI-50125 | K7A, L86E, N88C, R91D RNase I |
| QBI-50126 | K7A, L86E, N88R, G89D, R91D RNase I |
| QBI-50127 | R4C, K7A, L86E, N88C, R91D, V118C RNase I |
| QBI-50128 | R4C, K7A, L86E, N88R, G89D, R91D, V118C RNase I |

In some embodiments, EVADE ribonucleases are conjugated to molecules that accelerate their targeting to and uptake by diseased cells (e.g., cancer, viruses, autoimmune diseases). This type of modification extends the utility and enhances the efficacy of the EVADE ribonucleases. An EVADE ribonuclease that has been modified to carry a Cys at any amino acid can be readily adapted for use in this conjugation strategy. Amino acids in the loop region corresponding to amino acids 84-95 of bovine ribonuclease A are of particular interest for conjugation. A preferred conjugation partner is an antibody that binds to a cell-specific epitope (e.g. a cancer marker). The antibody is cross-linked to the EVADE ribonuclease via a non-cleavable or a cleavable cross-linker. A non-cleavable chemical cross-linker may include m-maleimidobenzoyl-N-hydroxysuccinimide ester (MBS). Alternatively, a cleavable linker may be used, with the cleavage occurring as a result of enzymatic activity (e.g., protease or a lactamase) or a change in environment (e.g., reducing or acidic environment). A number of chemistries are available for conjugation to an antibody, including an aldehyde (generated by oxidation of carbohydrate), an amine (present on the lysine side chains), or a thiol (particularly useful for conjugation to Fab' fragment or scFv).

| Ribonuclease | Antibody | Cross-linker category | Examples |
|---|---|---|---|
| thiol of Cys of EVADE ribonuclease | thiol of Fab′ fragment | bifunctional thiol | BMB (8.0 Å)<br>BMDP (10.2 Å)<br>BMOE (10.9 Å)<br>$BM(PEO)_3$ (14.7 Å)<br>$BM(PEO)_4$ (17.8 Å) |
| thiol of Cys of EVADE ribonuclease | non-native Cys of single chain (scFv) | bifunctional thiol | See above |
| thiol of Cys of EVADE ribonuclease | Thiol of mAb (introduced by reaction of small molecule with amines of mAb; e.g with iminothiolane) | bifunctional thiol | See above |
| thiol of Cys of EVADE ribonuclease | Amine of mAb | thiol, amine heterobifunctional | sulfo-GMBS (6.8 Å)<br>sulfo-SIAB (10.6 Å)<br>sulfo-EMCS (9.4 Å) |
| thiol of Cys of EVADE ribonuclease | Aldehyde of mAb | thiol, aldehyde heterobifunctional | BMPH (8.1 Å)<br>EMCH (11.82 Å)<br>KMUH (19 Å)<br>$M_2C_2H$<br>MPBH (17.9 Å) |
| thiol of Cys of EVADE ribonuclease | Amine of antibody | Thiol, amine heterobifunctional cleavable linker | PDPH |

A cleavable cross-linker of particular interest is made by incorporation of a protease sensitive peptide into the cross-linker. The protease, in some embodiments, is selected from a wide variety of naturally occurring enzymes, including endosomal and lysosomal proteases. Cathepsin B (a lysosomal cysteine protease of the papain family) expression is elevated in some cancerous cells, especially at the invasive edge of the tumor. Cathepsin B preferentially cleaves the Arg-Arg dipeptide, but is promiscuous in its substrate recognition. Furin is a cellular endoprotease that catalyzes the proteolytic maturation of proteins in the secretory pathway. Furin localizes predominately to the trans golgi network, but does travel to many cellular compartments, including endosomes, lysosomes, secretory granules, and the cell surface.

An alternative strategy is to use a cross linker that is sensitive to β-lactamase and administer the β-lactamse concomitantly with the targeted EVADE ribonuclease. There are several additional types of linkers that can be cleaved such as peptide bonds, disulfide bonds, hydrazones, and phosphodiesters. The present invention is not limited to the linkers discussed herein. One skilled in the art will appreciate that a variety of linkers will find use with the present invention.

Conjugating Antibodies:

Many different antibodies may be conjugated the EVADE ribonuclease to generate conjugates of the present invention. The CEA antigen is one of many known protein antigens that are over-expressed on the surface of cancer cells and has been used previously to create targeted therapeutics. Another antigen is CD33, which is present on acute myeloid leukemia cells. Acute myeloid leukemia (AML) is a cancer that may be treated by an anti-CD33 strategy. MYLOTARG is a CD33 antibody-calicheamicin conjugate approved for treatment of AML. CD22 is a cell surface receptor found on B-cells which can also be used for antibody-based therapeutics.

The targeted EVADE ribonucleases may also be made using antibodies against other cancer cell antigens. A variety of antibodies may be amenable to such a conjugation strategy. Among these, the preferred antigens of interest are:

- over-expressed on cancer cells relative to normal cells
- internalized by the cell (to facilitate ribonuclease entry into the cytosol)
- recognized by a monoclonal antibody The following examples describe conjugates of humanized M195 (huM195), an antibody specific for CD33 (Immunotoxin Resistance in Multidrug Resistant Cells. Cancer Res., 2003, 63, 72-79) and an EVADE ribonuclease QBI-50112 (R4C, L86E, N88C, R91D, V118C RNase I). The linkers are varied and include stable and cleavable linkers.

Non-Cleavable Linkers

Maleimide-Hydrazine

Carbohydrates found in the constant region of an antibody is oxidized to provide an aldehyde, which is reactive with hydrazine. The hydrazine of a cross-linker (BMPH, KMUH) is reacted with the aldehydes (oxidized carbohydrates) to form a hydrazone. The modified antibody then displays a maleimide, which is reacted with the free thiol in a protein to form an antibody-protein conjugate. Thioether formation takes place at neutral pH.

The carbohydrates of huM195 are oxidized with by treatment of the antibody with 10 mM sodium periodate at room temperature for approximately one hour at 4° C. The reaction is performed in the dark because sodium periodate is light sensitive. A desalting column (Amersham Biosciences, Sephadex G-25 Fine) is used prior to use of oxidized huM195 for conjugation. A solution of BMPH is added to the oxidized huM195, and the reaction allowed to proceed for 30-60 minutes at room temperature. The reaction is then applied to a desalting column (Amersham Biosciences, Sephadex G-25 Fine)

Reaction times, ratios of reagents, solution concentrations, and temperatures may be optimized to increase yield and purity of the conjugate. Fractions are collected, and their absorbance at 280 nm monitored. Once the maleimide-huM195 containing fractions are pooled, a solution of the EVADE ribonuclease variant QBI-50112 (20 mM sodium phosphate buffer, 0.15 M NaCl, pH 7.0 (PBS) with 10 mM EDTA) with a free cysteine residue is added in a one to one ratio with maleimide-huM195. The reaction is allowed to proceed for 30 minutes and then quenched by the addition of Tris buffer with cysteine. The conjugated sample is applied to a desalting column (Amersham Biosciences, Sephadex G-25 Fine) and eluted with buffer (10 mM sodium phosphate, 150 mM NaCl, pH 7.4). The fractions are monitored using the 280 nm absorbance. The product-containing (huM195-QBI-50112) fractions are pooled. Reaction times, ratios of reagents, solution concentrations, and temperatures may be optimized to increase yield and purity of the conjugate.

A

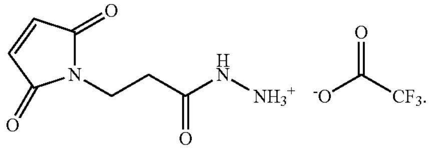

B

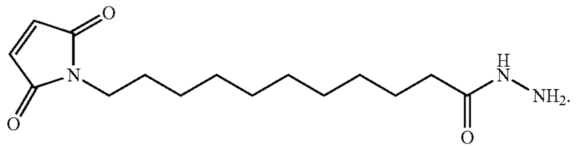

A. N-(β-maleimidopropionic acid) hydrazide•TFA (BMPH; 8.1 Å)
B. N-(κ-maleimidoundecanoic acid) hydrazide (KMUH; 19.0 Å)

Maleimide-NHS

The activated ester (an N-hydroxy succinimide) can be selectively reacted with amines in the antibody (typically lysine side chains) without affecting the maleimide. A covalent, chemically stable amide bond is formed. The modified antibody is then reacted with the single free thiol in the ribonuclease variant to form the conjugate. The reaction of the thiol of the ribonuclease variant with the maleimide is most selective at pH 6.5-7.5.

A four-fold excess of the crosslinker (EMCS or SMCC; Pierce) is dissolved in DMF (or DMSO if necessary) and is then added to a solution of huM195 in buffer (20 mM sodium phosphate buffer, 0.15 M NaCl, pH 7.0 (PBS)). The reaction is allowed to proceed for 30 minutes at 4° C. The reaction mixture is applied to a desalting column (Amersham Biosciences, Sephadex G-25 Fine). Fractions are collected, and their absorbance at 280 nm monitored. Once the maleimide-huM195 containing fractions are pooled, a solution of the EVADE ribonuclease variant QBI-50112 (20 mM sodium phosphate buffer, 0.15 M NaCl, pH 7.0 with 10 mM EDTA) with a free cysteine residue is added in a one to one ratio with maleimide-huM195. The reaction is allowed to proceed for 30 minutes and then quenched by the addition of Tris buffer with cysteine. The conjugated sample is applied to a desalting column (Amersham Biosciences, Sephadex G-25 Fine) and eluted with buffer (10 mM sodium phosphate, 150 mM NaCl, pH 7.4). The fractions are monitored using the 280 nm absorbance. The product-containing (huM195-QBI-50112) fractions are pooled. Reaction times, ratios of reagents, solution concentrations, and temperatures may be optimized to increase yield and purity of the conjugate.

A

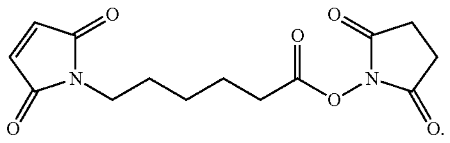

B

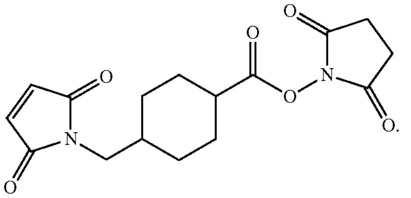

A. N-(ε-maleimidocaproyloxy) succinimide ester (EMCS; 9.4 Å)
B. Succinimidyl 4-(N-maleimido-methyl)cyclohaxane-1-carboxylate (SMCC; 11.6 Å)

α-Haloacetyl-NHS

The activated ester (an N-hydroxy succinimide) is selectively reacted with amines without affecting the haloacetyl. The optimal pH for the reaction is pH 7-9. The modified antibody is then reacted with the single free thiol in the ribonuclease variant to form the conjugate.

A solution of crosslinker (SBAP or SIAB) in DMSO is added to huM195 solution (0.1 M sodium phosphate, 0.15 M NaCl, pH 7.2) and allowed to react for approximately 30 minutes. The reaction mixture is be run over a desalting column (Amersham Biosciences, Sephadex G-25 Fine) with borate buffer (50 mM sodium borate, pH 8.3, 5 mM EDTA).

Fractions are collected, and their absorbance at 280 nm monitored. A solution of the EVADE ribonuclease variant QBI-50112 (R4C, L86E, N88C, R91D, V118C RNase I) is added, and the reaction of the single free thiol of the RNase with the haloacetyl sits for approximately one hour. These reactions are performed in the dark due to the potential for side products. The reactions are quenched by the addition of Tris buffer with cysteine. The quenching reaction is allowed to proceed for 15 minutes at room temperature in the dark. The conjugated sample is applied to a desalting column (Amersham Biosciences, Sephadex G-25 Fine) and eluted with buffer (10 mM sodium phosphate, 150 mM NaCl, pH 7.4 (PBS)). The fractions are monitored using the 280 nm absorbance. The product-containing (huM195-QBI-50112) fractions are pooled. Reaction times, ratios of reagents, solution concentrations, and temperatures may be optimized to increase yield and purity of the conjugate.

A

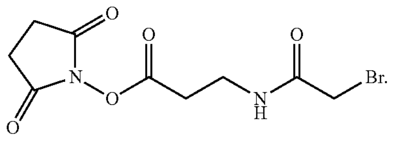

B

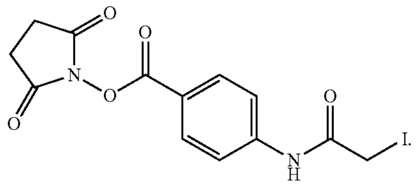

A. Succinimidyl 3-(bromoacetamido) propionate (SBAP; 6.2 Å)
B. N-Succinimidyl(4-iodoacetyl)aminobenzoate (SIAB; 10.6 Å)

Cleavable Linkers

These linkers are peptide-based and are be cleaved by a human protease. The example describes linkers cleaved by the protease furin. Furin recognizes Arg-Xaa-Yaa-Arg, where Xaa is unspecified and Yaa is Lys or Arg. Hydrolysis occurs after the C-terminal Arg.

The reactive groups (maleimide, hydrazine, N-hydroxy succinimide ester, α-halo acetyl) used in the protease-sensitive cross-linkers are the same as the commercially available linkers.

Peptides are dissolved in dd$H_2O$ and added at a 3-fold molar excess to a solution of huM195 (0.1 M sodium phosphate, 0.15 M NaCl, pH 7.2) and allowed to react for approximately 30 minutes. The reaction mixture will be run over a desalting column (Amersham Biosciences, Sephadex G-25 Fine) with borate buffer (50 mM sodium borate, pH 8.3, 5 mM EDTA). Fractions are collected, and their absorbance at 280 nm monitored. A solution of the EVADE ribonuclease variant QBI-112 in 20 mM sodium phosphate, pH 7.0, containing NaCl (0.15 M) and EDTA (0.01 M) is added. The reaction proceeds at room temperature with stirring. Under these conditions, reaction between the maleimide and a thiol is favored by 1000-fold over reaction between the maleimide and an amine. After 30 min, the reaction will be quenched by addition of a Tris-HCl buffer containing cysteine at a concentration 10-fold greater than that of the peptide substitutent. Peptides bearing the α-bromo-acetyl group are conjugated by using identical procedures, with three exceptions. Reactions are run in a 20 mM MOPS buffer, pH 8.2, containing NaCl (150 mM) and EDTA (0.1 mM) for 60 min at 37° C. in the dark. The conjugated sample is applied to a desalting column (Amersham Biosciences, Sephadex G-25 Fine) and eluted with buffer (10 mM sodium phosphate, 150 mM NaCl, pH 7.4). The fractions are monitored using the 280 nm absorbance. The product-containing (huM195-QBI-50112) fractions are pooled. Reaction times, ratios of reagents, solution concentrations, and temperatures may be optimized to increase yield and purity of the conjugate.

A

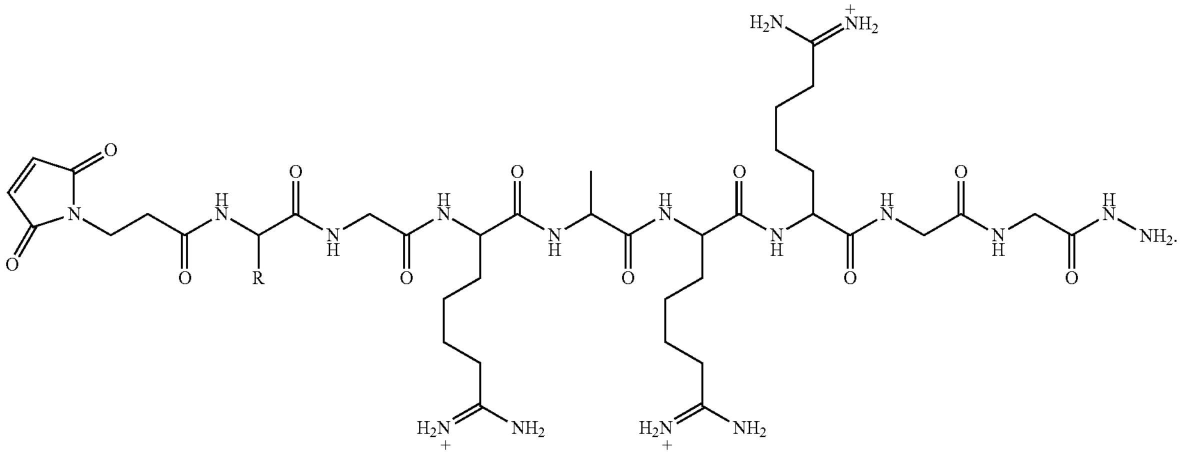

-continued

B

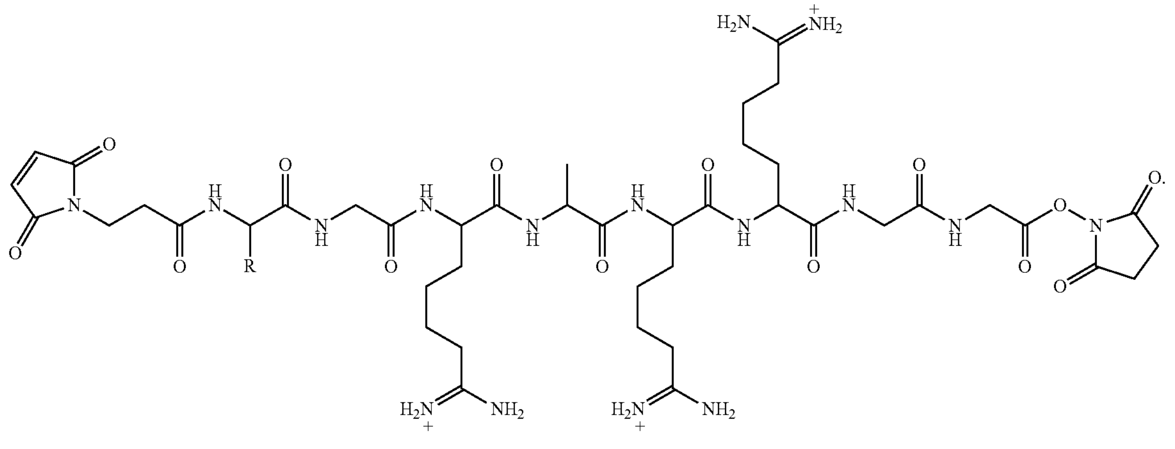

C

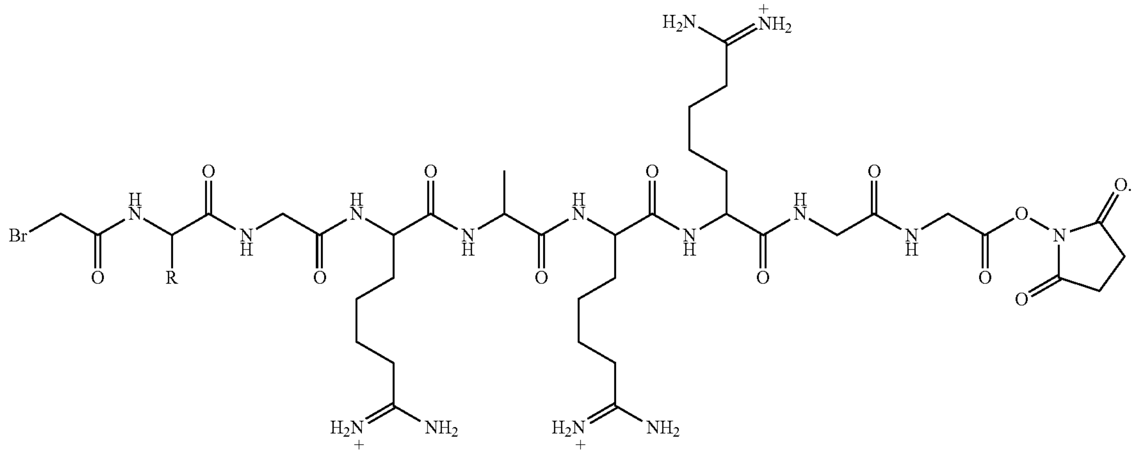

D

R =
H
$CH_2C_6H_5$
$CH_2CH_2CH_2CH_2C(NH_2)NH_2^+$
$CH_2CH_2CO_2H$.

A. Furin-sensitive maleimide-hydrazine cross-linker
B. Furin-sensitive maleimide-succinimide cross-linker
C. Furin-sensitive α-bromo acetyl-succinimide cross-linker
D. Identity of the R groups to be used in peptides A-C.

Fusion Proteins

The cDNA encoding an anti-CEA scFv fragment will be fused to the 5'-end of the cDNA encoding the EVade ribonuclease QBI-50110 (R4C, L86E, N88R, G89D, R91D, V118C RNase I) RNase. Six glycine residues will be incorporated between the scFv and the ribonuclease to minimize hindrance. The cDNA will be sequenced, cloned in *E. coli*, and expressed as an insoluble protein sequestered in inclusion bodies. The inclusion bodies will be denatured and refolded. After refolding, the fusion will be purified by standard protein chromatography methods, including size-exclusion and hydrophobic interactions. Production of the anti-CEA scFv-EVade fusion may be optimized to increase yield and/or purity.

The following reference, incorporated herein by reference in their entireties, describe various ribonucleases, targeting moieties, conjugation methods, pharmaceutical compositions, and treatment methods that find use in conjunction with the present invention: U.S. Pat. Nos. 3,627,876, 4,331,764, 4,882,421, 4,904,469, 5,200,182, 5,270,204, 5,286,487, 5,286,637, 5,359,030, 5,389,537, 5,484,589, 5,529,775, 5,540,925, 5,559,212, 5,562,907, 5,595,734, 5,660,827, 5,702,704, 5,728,805, 5,786,457, 5,840,296, 5,840,840, 5,866,119, 5,955,073, 5,973,116, 6,045,793, 6,051,230, 6,083,477, 6,175,003, 6,183,744, 6,197,528, 6,235,313, 6,239,257, 6,271,369, 6,280,991, 6,290,951, 6,312,694, 6,395,276, 6,399,068, 6,406,897, 6,416,758, 6,423,515, 6,541,619, 6,558,648, 6,649,392, 6,077,499, 4,888,172, 6,653,104, and U.S. Pat. Publ. Nos. US20020006379A1, US20020037289A1, US20020048550A1, US20020111300A1, US20020119153A1, US20020187153A1, US20030031669A1, US20030219785A1, US20020106359A1, and US20030148409A1.

Example 2

Tumor Growth Inhibition by QBI-119

This Example describes the use of RNase variant QBI-119 for tumor growth inhibition. QBI-119 is an RNA variant that is R4C, G38R, R39D, L86E, N88R, G89D, R91D, V118C RNase I. The in vivo efficacy of this RNase variant was determined using a standard xenograft model. In particular, A549 non-small human cancer cells (American Type Culture Collection Number CRL-1687) and Bx-PC-3 pancreatic cells (American Type Culture Collection Number CCL-185) were employed with athymic nude mice. Approximately $2\times10^6$ cells were implanted into the right rear flank of 5-6 week old male homozygous (nu/nu) nude mice (Harlan). Tumors were allowed to grow to an average size of ≥75 $mm^3$ before treatments were initiated. Animals of each tumor type, with the properly sized tumors, were divided into treatment groups, including one set of animals treated with vehicle (PBS) on the same dosing schedule as the treatment arm. QBI-119 was dosed at 15 mg/kg qd×5 (five times per week) throughout the course of the study. Tumors were measured twice weekly using calipers. Tumor volume ($mm^3$) was determined by using the formula for an ellipsoid sphere:

$$\text{volume} = \frac{l \times w^2}{2}$$

The percent tumor growth inhibition is determined using the following formula:

Percent tumor growth inhibition (% TGI)

-continued $$\%\ TGI = 1 - \frac{(\text{final size} - \text{starting size})_{treated}}{(\text{final size} - \text{starting size})_{control}} \times 100$$

Figure 2:
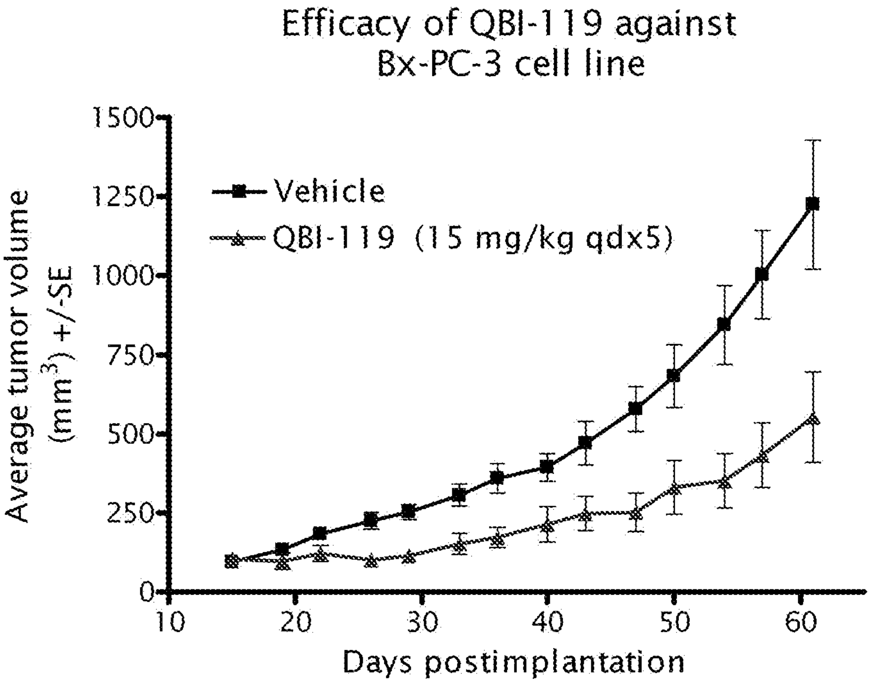
FIG. 2A shows a graph demonstrating the growth inhibiting effect of QBI-119 on tumor volume (Bx-PC-3 cells) over a number of days.
FIG. 2B shows a graph depicting the lack of toxicity of QBI-119.
Figure 2:
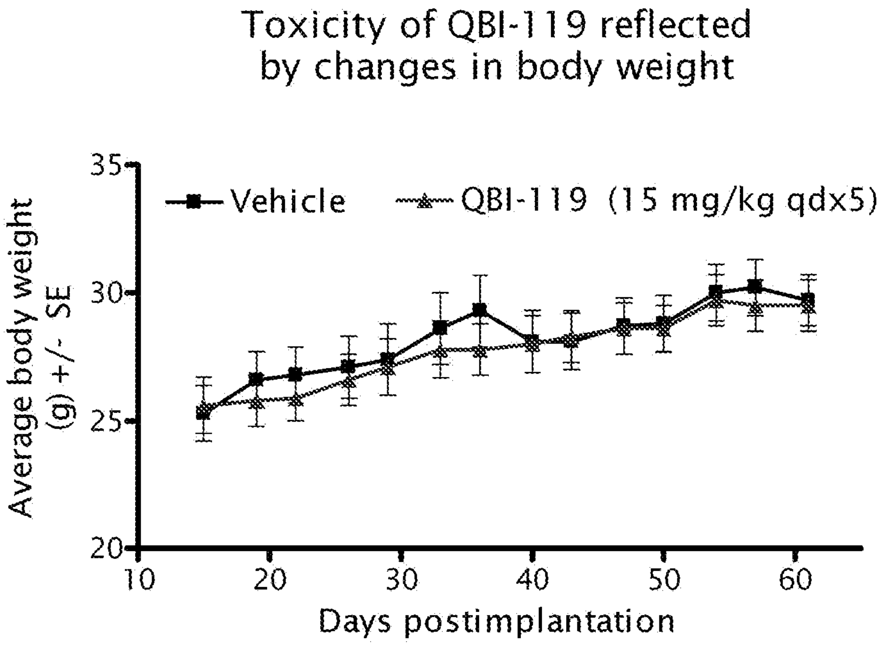

The results of this Example are shown in FIGS. 1-2. FIG. 1A shows the tumor growth inhibition caused by QBI-119 on A549 cells was significant (64%), while FIG. 1B shows that QBI-119 had no significant impact on animal weights at this dosage. FIG. 2A shows the tumor growth inhibition caused by QBI-119 on Bx-PC-3 cells was significant (60%), while FIG. 1B shows that QBI-119 had no significant impact on animal weights at this dosage.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. A composition comprising tumor-cell specific monoclonal immunoglobulin or functional fragment thereof conjugated to a variant of ribonuclease one (human RNase I) of SEQ ID NO:2, wherein said variant ribonuclease comprises an arginine at position 38, as well as:

a) two or more changes in region 86-91;

b) a change at position 39;

c) a change to a cysteine at a position 1-6; and d) a change to a cysteine at a position 116-121.

2. The composition of claim 1, wherein said variant ribonuclease has the biological property of cell killing or RNA degradation.

3. The composition of claim 1, wherein said monoclonal immunoglobulin comprises a human or humanized antibody.

4. The composition of claim 3, wherein said humanized antibody comprises the complementarity determining regions from mouse antibody variable regions fused to framework regions from human variable regions.

5. The composition of claim 1, wherein said monoclonal immunoglobulin comprises a functional antibody fragment.

6. The composition of claim 5, wherein said functional antibody fragment is a Fab fragment or a F(ab')2 fragment.

7. The composition of claim 1, wherein said monoclonal immunoglobulin is selected from the group consisting of IgG, IgA, IgM, IgD, IgE, and secreted immunoglobulins (sIg).

8. The composition of claim 1, wherein said antibody is a chimeric antibody.

9. The composition of claim 7, wherein said chimeric antibody comprises the variable regions of mouse antibody joined to human constant regions.

10. The composition of claim 1, wherein said antibody is a modified antibody.

11. The composition of claim 10, wherein said modified antibody comprises covalently modification of the antibody surface with polyethylene glycol (PEG).

12. The composition of claim 1, wherein said cell is a cancer cell.

13. The composition of claim 1, wherein said RNA is of viral origin.

14. The composition of claim 1, wherein said ribonuclease is conjugated to said cell- or disease-specific monoclonal immunoglobulin by a linker.

15. The composition of claim 14, wherein said linker is attached to a non-native cysteine of said ribonuclease.

16. The composition of claim 1, wherein said monoclonal immunoglobulin is conjugated to said ribonuclease within a region of said ribonuclease selected from the group consisting of the N-terminus, the C-terminus, a loop region and a turn region.

17. The composition of claim 1, wherein said ribonuclease and said monoclonal immunoglobulin comprise a fusion protein.

* * * * *